United States Patent [19]  [11] Patent Number: 5,586,085
Lichte  [45] Date of Patent: Dec. 17, 1996

[54] CONTAINER AND ADAPTOR FOR USE WITH FLUID VOLUME SENSOR

[76] Inventor: Leo J. Lichte, 3169 Mumford Ave., Riverside, Calif. 92503

[21] Appl. No.: 185,718

[22] Filed: Jan. 24, 1994

Related U.S. Application Data

[63] Continuation-in-part of Ser. No. 785,792, Oct. 31, 1991, Pat. No. 5,303,585, and Ser. No. 791,994, Nov. 14, 1991, Pat. No. 5,279,601.

[51] Int. Cl.$^6$ ........................................... G01F 23/00
[52] U.S. Cl. ........................... 367/99; 367/908; 367/165; 73/290 V
[58] Field of Search ..................... 367/908, 140, 367/99, 165; 73/290 V

[56] References Cited

U.S. PATENT DOCUMENTS

| | | | |
|---|---|---|---|
| 3,163,843 | 12/1964 | Dieckamp | 73/290 V |
| 3,237,451 | 3/1966 | Hoeff | 73/290 V |
| 3,326,042 | 6/1967 | Ross et al. | 73/290 V |
| 3,520,186 | 7/1970 | Adams et al. | 72/290 V |
| 3,603,149 | 9/1971 | McKown | 73/290 V |
| 3,839,651 | 10/1974 | Michaels | 73/290 V |
| 3,918,018 | 11/1975 | Tuley et al. | 73/290 V |
| 4,063,457 | 12/1977 | Zekulin et al. | 73/290 V |
| 4,130,018 | 12/1978 | Adams et al. | 73/290 V |
| 4,144,517 | 3/1979 | Baumoel | 73/290 V |
| 4,170,765 | 10/1979 | Austin et al. | 73/290 V |
| 4,210,969 | 7/1980 | Massa | 73/290 V |
| 4,221,004 | 9/1980 | Combs et al. | 369/114 |
| 4,229,798 | 10/1980 | Rosie et al. | 73/290 V |
| 4,305,405 | 12/1981 | Meisch | 128/782 |
| 4,320,659 | 3/1982 | Lynnworth et al. | 73/290 V |
| 4,343,316 | 8/1982 | Jespersen | 128/771 |
| 4,448,207 | 5/1984 | Parrish | 73/290 V |
| 4,474,061 | 10/1984 | Parker | 73/290 V |
| 4,535,627 | 8/1985 | Prost et al. | 73/149 |
| 4,572,253 | 2/1986 | Farmer et al. | 367/908 |
| 4,623,976 | 11/1986 | Carp et al. | 364/571.07 |
| 4,651,555 | 3/1987 | Dam | 73/290 V |
| 4,733,381 | 3/1988 | Farmer et al. | 367/93 |
| 4,770,038 | 9/1988 | Zuckerwar et al. | 73/290 V |
| 4,865,073 | 9/1989 | Kocher | 73/290 V |
| 4,912,686 | 3/1990 | Craster | 73/290 V |
| 4,939,457 | 7/1990 | Tellerman | 73/314 |
| 4,991,433 | 2/1991 | Warnaka et al. | 367/908 |
| 5,027,655 | 7/1991 | Sweet | 73/290 V |
| 5,301,549 | 4/1994 | Sinclair | 73/290 V |
| 5,319,973 | 6/1994 | Crayton et al. | 73/290 V |
| 5,323,361 | 6/1994 | Elle et al. | 367/98 |

FOREIGN PATENT DOCUMENTS

| | | | |
|---|---|---|---|
| 231518 | 11/1960 | Australia | 73/290 V |
| 3703658 | 2/1987 | Germany | 73/290 V |
| 3703658 | 8/1988 | Germany | 73/290 V |

OTHER PUBLICATIONS

Kharitonov et al., "Device for measuring the urine flow rate", *Biomed. Eng.*, vol. 11, No. 2, pp. 104–106 (Mar.–Apr. 1976).

Condon, Robert E., "Measurement of hourly urine output in a closed system", *Surgery*, vol. 56, No. 2, pp. 378–379 (Aug. 1964).

*Primary Examiner*—J. Woodrow Eldred
*Attorney, Agent, or Firm*—Knobbe, Martens, Olson & Bear, LLP

[57] ABSTRACT

A container having affixed thereto an ultrasonic transducer, including a connection for electrically linking the transducer to electronic circuitry located outside the container. Flexible and semi-rigid containers having rigid structures surrounding the signal path of an ultrasonic transducer are also provided. In addition, adaptors are disclosed for use in connecting an ultrasonic transducer to a container. Such adaptors can include a rigid tubular member, a tubular outlet connected to the tubular member for draining liquid from a container, and a seat for engaging an ultrasonic transducer.

30 Claims, 14 Drawing Sheets

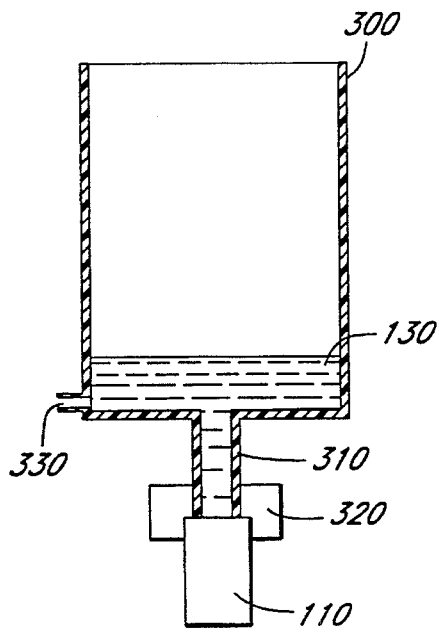
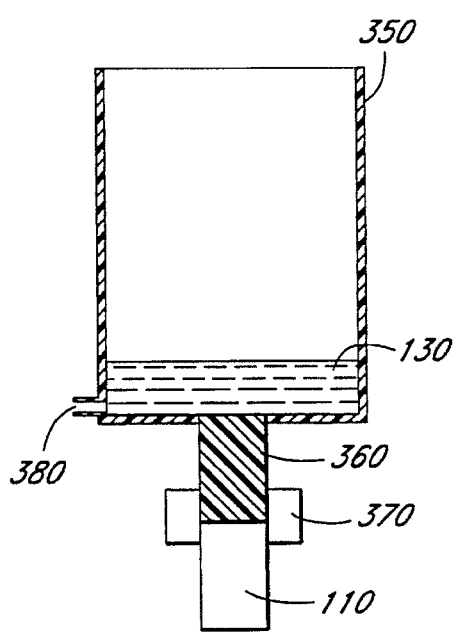
FIG. 4a     FIG. 4b
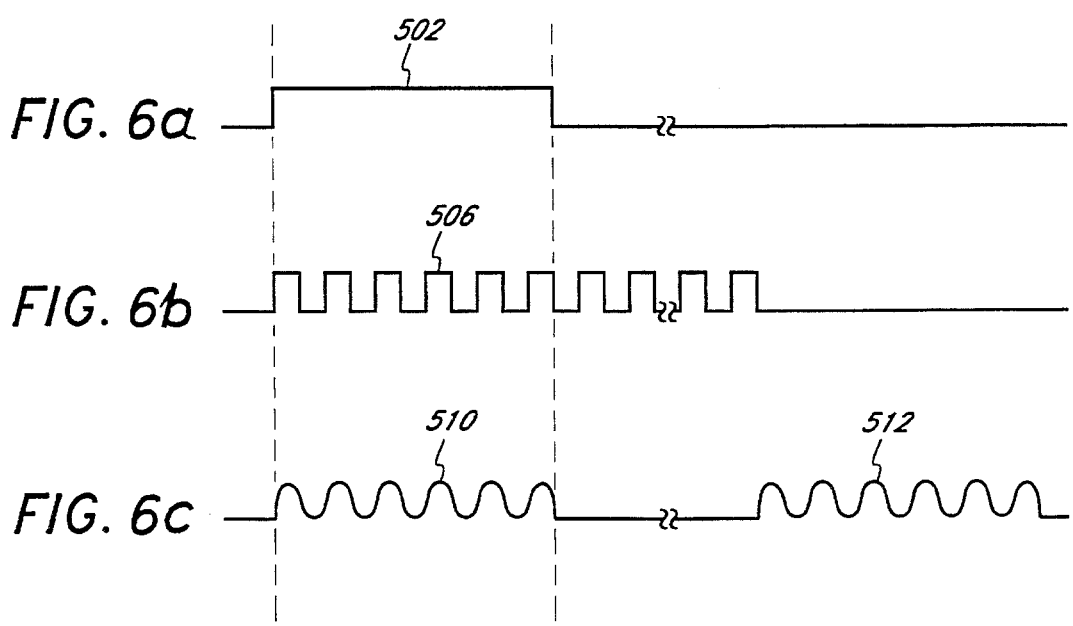
FIG. 6a
FIG. 6b
FIG. 6c

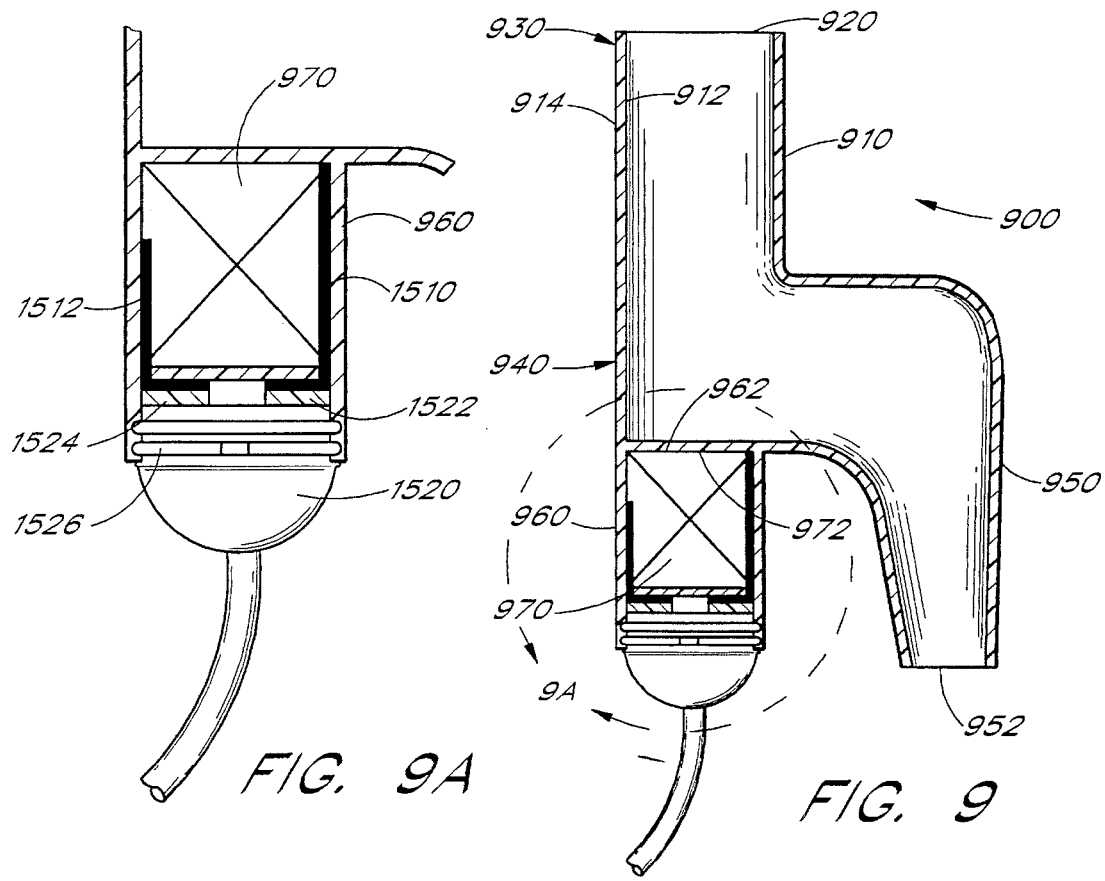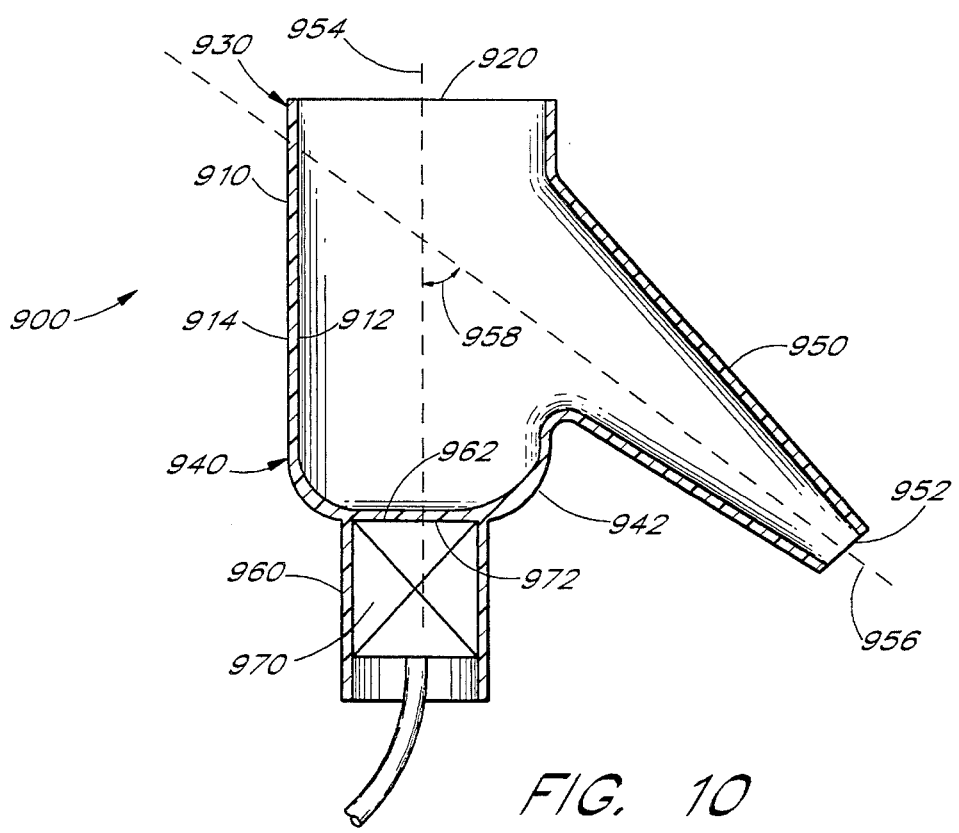

CONTAINER AND ADAPTOR FOR USE WITH FLUID VOLUME SENSOR

The present application is a continuation-in-part of a prior patent application entitled "Fluid Volume Sensor" filed on Oct. 31, 1991 and having Ser. No. 07/785,792 U.S. Pat. No. 5,303,585. The present application is also a continuation-in-part of a prior patent application entitled "Water Seal Water Manometer" filed on Nov. 14, 1991 and having Ser. No. 07/791,994 U.S. Pat. No. 5,279,601. The disclosures of these prior patent applications which are not otherwise contained in the present application are hereby incorporated by reference.

FIELD OF THE INVENTION

The present invention relates to novel containers used in conjunction with ultrasonic fluid volume sensors. Also included are adaptors for securing such fluid volume sensors to liquid containers.

BACKGROUND OF THE INVENTION

In a variety of applications, it is desirable to be able to determine the remaining volume of liquid in a container. In the medical field, for example, it is desirable to be able to determine the volume of reagent remaining in a source container used in automated clinical instrumentation. Determining the volume of saline or other liquid which remains in an intravenous infusion would also be advantageous.

A variety of means have been devised for permitting an attending physician or staff member to estimate the remaining liquid volume in a container. In the most basic form, containers have been provided with transparent walls and a graduated scale which is visible from the outside. However, the visual observation of liquid level is not always practical, such as when the container is not readily within the clinician's view. In addition, in some applications it may be desirable to have a more precisely quantitative indication of remaining liquid level or volume.

Thus, a variety of electronic liquid level detectors have been devised in the prior art. For example, U.S. Pat. No. 4,063,457 to Zekulin, et al. discloses an ultrasonic sensing device for mounting within a storage vessel such as a bilge or railroad tank car. The sensing device comprises an elongate tubular body to be vertically oriented within the tank car, having a port at the lower end to allow liquid to enter the tube and rise to the level of the liquid in the rest of the tank. Spaced apart vertically within the tube are a series of pairs of piezoelectric transducers which serve as transmitters and receivers of ultrasonic energy. Because ultrasonic energy propagates more readily through liquid than through air, the system can determine which pairs of piezoelectric transducers are below the liquid level and which pairs of piezoelectric transducers are above the liquid level. Thus, each piezoelectric pair serves to determine simply the presence or absence of liquid at that level.

Another submersible probe-type liquid level indicator is disclosed in U.S. Pat. No. 3,163,843 to Dieckamp. In this device, mechanical vibrations are propagated axially from a transducer through the probe which extends vertically within the liquid to be measured. Reflected transverse pulses are created at both the liquid surface and the submerged distal end of the probe, which are smaller in amplitude than the applied pulse. These reflected transverse pulses are propagated back to the transducer, and the waveforms of the various pulses are evaluated on an oscilloscope to determine the liquid level.

Another approach is disclosed in U.S. Pat. No. 4,144,517 to Baumoel. That patent discloses an externally mounted single transducer liquid level detector in which the presence or absence of liquid at a particular location of a tank or pipe is sensed through the wall of the container. The transducer can be secured to the outer surface of the container, such as by hand pressure, clamping or cementing. By comparing the rate of decay of the test signal following multiple wall reflections to known rate of decay values for filled and empty regions of the container, an output signal is produced which indicates the presence or absence of liquid in the container adjacent the transducer location.

In German Patent Application Number 3,703,658 to Schreiber, an ultrasonic signal is used to measure the level of liquid in a fuel tank for motor vehicles. Notwithstanding the foregoing, there remains a need for an improved volume sensor device which can be included in or externally mounted to a container and which can provide remaining liquid volume data on a continuous basis from empty through full. There also remains a need for adaptors for such volume sensor devices and for improved containers with which such devices can be used.

SUMMARY OF THE INVENTION

In one aspect, the present invention comprises a container for liquids having a seat in the lower end of the container and an ultrasonic transducer affixed to and in ultrasonic communication with the seat. The transducer is positioned in the seat such that an ultrasonic signal generated by the transducer travels approximately perpendicular to the surface of a liquid in the container, when a liquid is present in the container. This container further comprises a reversible connection which provides an electrical link between the ultrasonic transducer of the container and externally located electronic circuitry. This electronic circuitry is, of course, capable of directing the transducer to generate an ultrasonic signal. Preferably, the transducer and the reversible connection are integrally molded into the container, and more preferably the transducer is embedded in the container. In this embodiment the container can be made, for example, from a plastic material. The reversible connection can also comprises a plug and socket.

In another aspect, the present invention can comprise a flexible container for liquids which is adapted for use with an ultrasonic level or volume sensing device. The container, which has an upper end and a lower end, comprises a seat for engaging an ultrasonic transducer in its lower end. A hollow member, having an interior and an exterior, is positioned above the seat inside the container. This hollow member is rigid and encompasses an ultrasonic signal path on the interior of the hollow member between the lower end of the container and the upper end of the container. The hollow member extends from the lower end of the container to the upper end of the container but at the same time permits fluid communication between the interior of the hollow member and the exterior of the hollow member.

In yet another aspect of the present invention, a semi-rigid container for liquids is provided which is adapted for use with a volume or level sensing device comprising an ultrasonic transducer. The container, having an upper end and a lower end, comprises a rigid wall, a flexible wall, and a seat. The rigid wall, which is attached to the flexible wall, extends from the lower end of the container to the upper end of the container. The seat, in the lower end of the container, is adapted to engage an ultrasonic transducer.

The semi-rigid container of this aspect of the present invention also includes a means for providing an ultrasonic signal path from the lower end of the container to the upper end. In one embodiment, this means can comprise a hollow member which has an interior and an exterior and which is positioned above the seat inside the container. Such a hollow member is preferably rigid and extends from the lower end of the container to the upper end of the container in order to encompass an ultrasonic signal path. This hollow member permits fluid communication between the interior of the hollow member and the exterior of the hollow member.

In an alternate embodiment, an ultrasonic signal path can be provided by means of rigid ribs located on the rigid wall. The rigid ribs extend from the lower end of the container to the upper end of the container and encompass an ultrasonic signal path in the space between the ribs. In a further embodiment, the rigid wall is substantially flat and comprises a recessed area extending from the lower end of the rigid wall to the upper end of the rigid wall. The recessed area provides an ultrasonic signal path for the semi-rigid container.

A further aspect of the present invention comprises an adaptor used for mounting an ultrasonic transducer onto a port in a liquid container. Such a container would have an upper end and a lower end, and the port would be located in the lower end of the container. The adaptor would be connected to the port by means of a central hollow member, preferably by contacting the inner surface of the port receiving end of the central hollow member with the outer surface of the port. This central hollow member is preferably tubular in shape and in addition has a transducer receiving end.

The central hollow member of the adaptor of this aspect of the invention further includes a seat for engaging an ultrasonic transducer. This seat has an outer surface for contacting such a transducer, and when the container to which the adaptor is connected contains a liquid, the outer surface of the seat for the ultrasonic transducer should be substantially parallel to the surface of the liquid in the container. In one embodiment, the transducer is attached to the seat by means of a mechanical fitting, such as a bayonet fitting or threads which engage complementary grooves on the transducer. In alternate embodiments, the transducer can be attached to the seat by means of a pressure sensitive adhesive, an epoxy glue, or a hot-melt thermoplastic. Coupling gel or a resilient deformable material, such as latex, can be positioned between the transducer and the seat can in order to ensure intimate contact between the transducer and the seat.

In a further embodiment, the transducer can be reversibly secured to the seat by means of a magnetic material. Preferably, the seat contains two or more magnets, of which at least one is of opposite polarity compared to the other magnet or magnets in the seat. In this embodiment, the seat can contain a plurality of magnets in a predetermined configuration. In this case, the face of the transducer would also contain a plurality of magnets. The configuration of the plurality of magnets of the transducer is the mirror image of the predetermined configuration of the magnets in the seat, so that each magnet of the transducer can align with a magnet of opposite polarity on the seat when the seat is contacted with the face of the transducer. Yet a further embodiment of the invention can comprise a transducer embedded in the seat of the adaptor. In this embodiment, the adaptor is preferably linked to the electronic processing and control circuitry of the fluid volume sensor by means of a reversible electrical connection.

The adaptor in this aspect of the present invention further includes a medial hollow member, preferably tubular in shape, which comprises an adaptor connecting end and a distal end. The adaptor connecting end is connected to the central hollow member so that the medial hollow member and the central hollow member are in fluid communication. The medial hollow member is also preferably connected to the central hollow member at a point on the central hollow member between the port receiving end of the adaptor and the seat for engaging the ultrasonic transducer. Furthermore, the distal end of the medial hollow member is preferably adapted to be connected to a flexible tube.

In one embodiment, the medial hollow member extends from the central hollow member at an angle of 90 degrees or less with respect to the transducer receiving end of the central hollow member. In an alternate embodiment, the medial hollow member extends at an angle of 45 degrees of less with respect to the transducer receiving end of the central hollow member. In yet another embodiment, the medial hollow member extends from the central hollow member at an angle of 15 degrees or less with respect to the transducer receiving end of the central hollow member.

In order to eliminate the formation of bubbles and the like which may interfere with the signal of an ultrasonic transducer in the adaptor, a debubbling screen can be positioned in the central hollow member of the adaptor. However, alternative designs of the adaptor can also be used to protect the operation of an ultrasonic sensor from interference by gas bubbles. For example, the medial hollow member can be connected to the central hollow member at a point which is distal to the seat in the central hollow member, thereby creating a pocket of non-turbulent liquid between the medial hollow member and the seat when said central hollow member contains a liquid. A shield extending upward from the seat on the interior of the central hollow member can also be used to protect the ultrasonic signal path from interference by gas bubbles by encompassing at least a part of the signal path. Alternatively, the outer surface of the seat can be positioned in the central hollow member distally with respect to the transducer receiving end of the central hollow member, thereby raising the beginning of the ultrasonic signal path over the area in the adaptor which is likely to experience bubble formation. In addition, channel guides extending from the inner surface of the central hollow member can be used to minimize and contain turbulence which arises in the central hollow member.

The adaptor can additionally comprise a flexible sleeve, wherein the inner surface of the port-receiving end of the central hollow member is attached to the outer surface of the flexible sleeve. In an alternate embodiment, the outer surface of the port-receiving end of the central hollow member is attached to the inner surface of a flexible sleeve. In both of these embodiments, the flexible sleeve is hollow and is adapted to engage the port.

The adaptor can preferably be mounted onto a container which is a component of a medical device, such as a autotransfusion device. The container to which the adaptor is mounted typically contains liquids used in the therapeutic treatment of a mammal or liquids which are removed from a mammal.

In a further aspect, the present invention comprises a method for determining the change in the volume of a liquid in a container having a predetermined configuration, an inlet port through which liquid enters, and an outlet port through which liquid leaves the container. This method comprises the steps of a) generating an ultrasonic signal which propagates through the liquid and is subsequently received by a receiver;

b) measuring the time elapsed between the generation and reception of the ultrasonic signal;

c) converting the elapsed time between the generation and reception of the ultrasonic signal into a first volume measurement representing the volume of said liquid within said container;

d) repeating steps (a) to (c) after a specified period of time in order to produce a second volume measurement; and e) determining the change in the volume of said liquid in said container over said specified time period by comparing said first volume measurement and said second volume measurement.

The ultrasonic signal of this method can be generated by one transducer and received by a second transducer, or in the alternative can be generated and received by only a single transducer.

In order to determine the volume of a liquid which flows into a container with the fluid volume sensor system of the present invention, the following steps can be performed in addition to the steps of the foregoing method:

determining the rate at which the liquid flows out of the container;

multiplying the rate by the specified period of time, thereby determining the amount of the fluid which flows out of the container during the specified period of time; and adding the amount of the fluid which flows out of the container during the specified period of time to the change in the volume of the liquid over the specified period of time, thereby determining the volume of the liquid which flows into the container during the specified period of time.

When the volume of liquid which has flowed into the container over the specified period of time has been calculated, this volume can be displayed, such as with an LCD screen or by printing out the volume information in either numerical or graphical form.

The volume of liquid which flows out of a container can also be calculated using the foregoing method, by further performing the steps of:

determining the rate at which the liquid flows into the container;

multiplying the rate by the specified period of time, thereby determining the amount of the fluid which flows into the container during the specified period of time; and adding the amount of the fluid which flows into the container during the specified period of time to the change in the volume of the liquid over the specified period of time, thereby determining the volume of the liquid which flows out of the container during the specified period of time.

The volume of liquid which has flowed out of the container during the specified period of time can also be displayed, such as with an LCD screen or by printing out the volume information in either numerical or graphical form.

In a further embodiment of the foregoing method, steps (a) through (c) are repeated a plurality of times. These steps are repeated after the specified period of time, and a volume measurement is produced each time that these steps are repeated, thereby producing a plurality of volume measurements. In this way, the change in the volume of the liquid can be determined after each of the plurality of times that steps (a) through (c) are repeated. The plurality of volume measurements which are determined in this embodiment are advantageously displayed, such as through printing a graphical representation of the plurality of volume measurements, thereby showing the change in the volume of the liquid over the specified time interval.

In another aspect of the present invention, a method of actuating a pump which is draining liquid from a container is provided. This method generally comprises the steps of:

generating an ultrasonic signal which propagates through a liquid in the container and is subsequently received by a receiver;

measuring the time elapsed between the generation and reception of the ultrasonic signal;

converting the elapsed time between the generation and reception of the ultrasonic signal into a volume measurement representing the volume of the liquid within the container; and actuating the pump when the volume measurement reaches a predetermined level.

In this method, the step of actuating the pump can comprise, for example, turning off the pump, such as when the liquid level in the container approaches empty. The actuating step can also however comprise changing the flow rate of the pump. Preferably, the liquid which is present in the container is one which is used in the therapeutic medical treatment of a mammal, such as a human being.

In yet another aspect of the present invention, a method of activating an alarm in response to volume measurement data is provided, where such data relates to the volume of a liquid in a container. This method comprises the steps of:

generating an ultrasonic signal which propagates through the liquid and is subsequently received by a receiver;

measuring the time elapsed between the generation and reception of the ultrasonic signal;

converting the elapsed time between the generation and reception of the ultrasonic signal into a volume measurement representing the volume of the liquid within the container; and activating the alarm when the volume measurement reaches a predetermined level.

Preferably, the liquid which is present in the container in this aspect of the invention is one which is used in the therapeutic medical treatment of a mammal, such as a human being.

BRIEF DESCRIPTION OF THE DRAWINGS

FIGS. 4a and 4b are cross-sectional views of two possible configurations of the container which provide for a longer pulse duration time.

FIGS. 6a–6c are timing diagrams which show the waveshape and relative timing of certain signals produced by the electronics within the volume sensing system.

FIG. 9 is a cross-sectional view of one embodiment of the adaptor.

FIG. 9A is an enlarged cross-sectional view of the portion of the adaptor of FIG. 9 which is encompassed by the dashed line in FIG. 9.

FIG. 10 is a cross-sectional view of an alternate embodiment of the adaptor.

DETAILED DESCRIPTION OF THE INVENTION

I. Fluid Volume Sensors

In accordance with one aspect of the present invention, an ultrasonic sound signal is utilized to determine the volume or level of a liquid in a container. It is known that certain solid materials and liquids are permeable to frequencies of sound in the ultrasonic range. Gases, however, are relatively impermeable to sound waves in this range. Therefore, when an ultrasonic signal is propagated through a liquid, that signal will be reflected back into the liquid when it meets an interface between the liquid and a gas (air or any other gaseous medium).

The fluid volume sensors of the present invention take advantage of this phenomenon to determine the level or volume of a liquid in a container by sending an ultrasonic signal from the bottom of a container to the surface of a liquid in that container and then detecting that signal when it is reflected back from the surface of the liquid. As used herein, the term "fluid" denotes a liquid material, unless a different usage is apparent in context. The fluid volume sensors of the present invention thus determine the volume and/or level of liquid material in a container.

Figure 1:
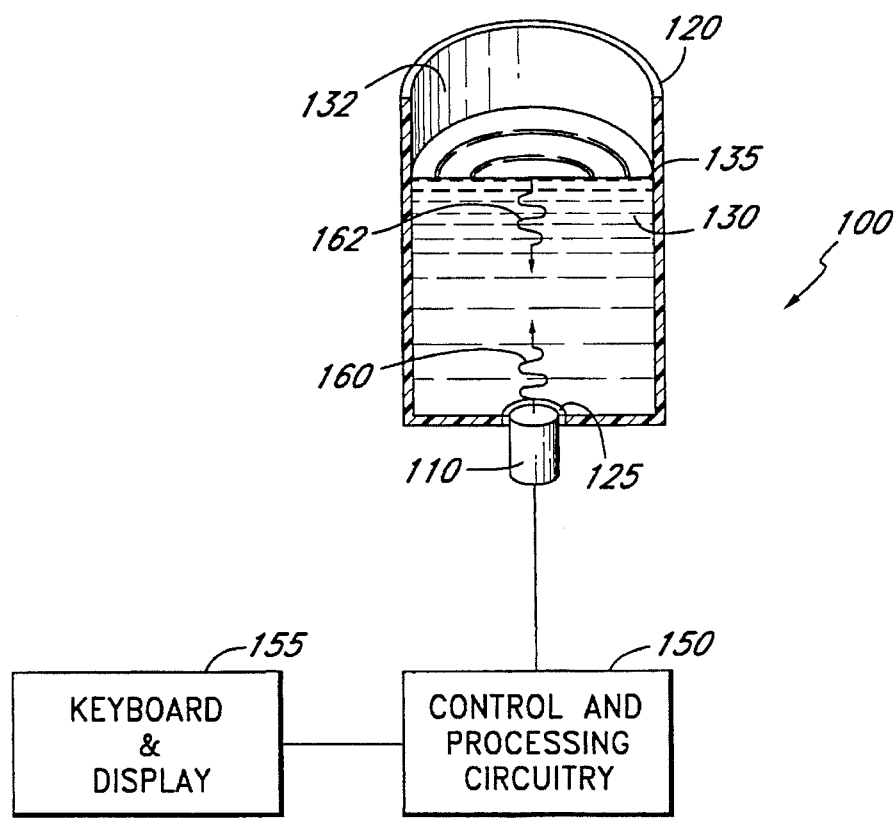
FIG. 1 is a simplified schematic diagram which shows the basic configuration of a volume sensing system constructed in accordance with the present invention.

FIG. 1 is a simplified schematic diagram which shows the basic configuration of a fluid volume sensor system 100 constructed in accordance with the present invention. The fluid volume sensor system 100 includes an ultrasonic transducer 110 which, in the embodiment shown in this Figure, is affixed to the lower end of a container 120 by means of an adaptor 125. The container 120 is constructed to hold a liquid 130. The liquid 130 does not fill the entire volume of the container 120, and a gas 132 (e.g., air) fills the remaining volume within the container 120. A gas-liquid boundary 135 is therefore formed within the container 120. The transducer 110 is electrically connected to control and processing circuitry, which is functionally designated by the control and processing circuitry box 150 (the control and processing circuitry 150 will be described in greater detail with reference to FIGS. 5 and 6 below).

In a preferred embodiment, the control and processing circuitry 150 includes a microprocessor or other processing device which can be connected with a keyboard and display interface 155, or with a dedicated system in a medical instrument so that a user can program and/or manually interact with the system 100. Thus, the volume sensor system 100 can act as a "stand alone" module. In one embodiment, the control and process circuitry 150 can be connected to a host computer system (not shown) such as an IBM PC, AT, etc., which can be employed to provide additional information storage and/or interface capability.

The transducer 110 is utilized to generate ultrasound pulses 160 and to detect reflected pulses 162 from the liquid-gas interface boundary 135. Of course, separate transducers (not shown in the Figures) for generating and receiving ultrasound pulses 160 can also be used. Such transducers can be produced in any of a variety of ways, which will be understood by one of skill in the art. In one embodiment, a ceramic crystal (not shown) is encased in a protective material such as epoxy to provide the transducer assembly 110. Suitable ceramic crystals are obtainable from EDO Corporation Electro-Ceramic Division, and sold under the model number AD-1259-.325; material: EC-70 Type V.

In order to hold the crystal securely within the transducer housing, any epoxy having minimal or optimally no gaseous inclusions can be employed. It has been found, however, that the performance of the crystal can be slightly improved by forming a small air gap within the epoxy directly behind the crystal.

The transducer assembly 110 is attached to the bottom of the container 120 in such a way that the side of the crystal that oscillates (the face of the crystal) is in sufficient sonic communication with the container 120 to provide an ultrasonic coupling. This contact can be achieved by permanent means or by temporary means, as long as the material used to obtain that contact contains minimal or no gaseous inclusions. Materials having gaseous inclusions, such as foamed materials, tend to dampen propagation of the signal. In addition, where mechanical means, such as clamping, are used to secure the transducer 110 to the container 120 in place of epoxy, a coupling medium layer such as glycerine or silicone oil can be placed between the transducer 110 and the container 120. Flexible materials such as elastomers and rubber can also be placed between these elements, as is known in the art. In one embodiment, the contacting face of the transducer assembly 110 is approximately one-half inch in diameter.

Although the adaptor 125, container floor, and any other media which separates the crystal face from the liquid 130 can be any of a wide variety of materials, materials should optimally be selected having sufficient acoustic qualities that they do not excessively dampen the ultrasonic pulse 160 as it propagates through the materials. Ideally, the natural frequency of the crystal is about 2.0 to 2.5 megahertz, although frequencies in the range of 1 megahertz to 5 megahertz can have applications.

The electronic circuitry 150 is provided to excite the crystal at a known frequency for short pulses, as is well known in the art. By applying a voltage across the crystal at the proper frequency, the crystal is excited so that it vibrates in accordance with an effect known as the piezo-electric effect. This vibration produces a sharp ultrasonic pulse 160. The pulse 160 is then transmitted through the container 120 and into the liquid 130 in the system shown in FIG. 1.

The transducer 110 receives control signals from the circuitry 150, which causes the transducer 110 to emit the ultrasonic pulse 160. In one embodiment, the frequency of the emitted pulse 160 is advantageously on the order of 3 MHz. The pulse 160 propagates vertically through the liquid 130, but generally does not propagate well through the gas 132. Instead, most of the ultrasonic energy of the pulse 160 is reflected back from the liquid-gas boundary 135 so that an "echo" pulse 162 is created. For example, as shown in FIG. 1, the pulse 160 is an example of an ultrasonic pulse which has just been generated by the transducer 110, while the pulse 162 is an example of an ultrasonic "echo" pulse which has been reflected from the liquid-gas boundary 135.

The "echo" pulse 162 propagates back through the liquid 130 to the transducer 110, where the pulse 162 is detected and converted into an electrical signal. In order to prevent interference between the propagated and reflected ultrasonic pulses 160, 162, the pulse 160 should have a dwell time sufficient to allow the transmitted pulse 160 to return from (bounce off of) the liquid-gas boundary 135 and be received by the same crystal after generation of the transmitted pulse 160 has ceased, and before a new pulse is generated.

When the crystal receives the returned "echo" pulse 162, it reacts by oscillating. The oscillation of the crystal is then converted to a voltage signal readable by the electronic circuitry 150. The voltage signal is transmitted to the circuitry 150 where it is analyzed and processed to determine the volume of the liquid 130 within the container 120.

When determining the volume of the liquid 130 within the container 120, the duration between the transmittal of the pulse 160 and the reception of the reflected return pulse 162 is measured. If the velocity of the transmitted ultrasonic pulse 160 is known, the measured duration can be converted into a distance value which represents the distance that the pulse traveled. The distance value can be converted into a number of different value units such as inches or centimeters, etc., or simply an internal, machine-readable value. The measurement of the duration between the transmittal and reception of the ultrasonic pulse 160, as well as the conversion of the measured duration into a distance value is advantageously accomplished by means of the control and processing circuitry 150.

As stated above, when the velocity at which the ultrasonic pulse 160 propagates through the liquid 130 is known, the distance between the liquid-gas interface 135 and the transducer 110 can be calculated using the duration measurement. The velocity at which the pulse 160 propagates through the liquid 130 can be determined using a calibration procedure in which a test pulse is generated by the crystal, reflected at the liquid-gas boundary 135, and received by the crystal within the transducer 110. The time between the transmission and reception of the test pulse is then measured. Finally, the actual distance between the crystal within the transducer 110 and the liquid-gas boundary 135 is measured precisely. This measured distance, of course, would also take account of the thickness of any solid material that is used to attach the transducer 110 to the container 120 and/or the thickness of the container material.

The velocity of an ultrasonic pulse within the liquid 130 can then be calculated using the measured values of the time between the transmission and reception of the test pulse, and the measured distance between the crystal and the liquid-gas boundary 135. By means of this calibration technique, variations in the propagation velocity of the pulse 160 due to temperature changes in the liquid 130, composition changes of the liquid 130, etc., can be accounted for. Once a calibrated pulse propagation velocity value has been obtained, the distance value can be calculated by simply multiplying the velocity value by half of the duration value.

Since velocity varies as a function of both temperature and liquid density, accuracy is optimized if calibration occurs under conditions which are similar to the actual use environment. In one preferred application of the present invention, the invention is utilized to determine liquid volume in a reservoir for receiving blood drained from the chest cavity of a patient recovering from open heart surgery. The normal physiologic temperature of human blood is approximately 37° C., and open heart surgery is typically conducted at any of a variety of reduced temperatures. In certain procedures, blood or other liquids could be reduced to as low as about 4° C. In addition, when returning blood from a reduced temperature back to 37° C., the blood will frequently be heated slightly above normal to approximately 40° C.

Thus, to accommodate the changes in viscosity which occur over the range of temperatures experienced in this application, the apparatus of the present invention is provided with a sensor and with circuitry to automatically measure the temperature of the liquid and to adjust for the time differences in the propagated signal which occur as a result of changed viscosity at different temperatures. The instrument will typically be calibrated at the point of manufacture throughout the range of from about 2° C. to about 45° C. in approximately 5° increments.

With the foregoing techniques, the distance from the fluid volume sensor to the surface of a liquid material in a container can be determined. This, however, only gives information to a user as to the level of fluid in the container. Advantageously, the volume of the liquid in the container is also determined. In accordance with the present invention, the volume of the container 120 can be determined from the acquired distance value by a number of different techniques. For example, if the container's exact configuration and dimensions are known, the volume of the container 120 can be determined mathematically as a function of the level of the liquid 130 (i.e., the distance value). If, however, the container 120 is irregularly shaped, the volume of the liquid 130 within the container 120 can be determined empirically by means of a calibration procedure which, in one embodiment, employs a "look-up" table within the circuitry 150.

Figures 2A, 2B, 2C:
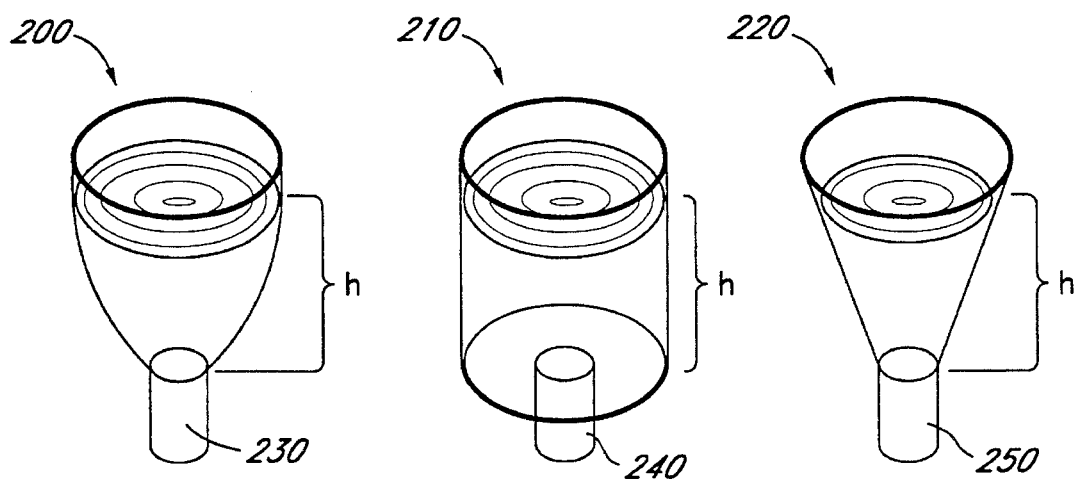
FIGS. 2a–2c show three different regular container configurations having an easily calculable height to volume correlation.

If the container 120 has a known configuration which can readily be described mathematically as a function of the level of the liquid 130, then the appropriate mathematical formula can be programmed into the process and control circuitry 150, and the volume of the liquid 130 within the container 120 can be calculated as a function of the level (or height) of the liquid 130 from the base of the container 120. For example, FIGS. 2a–2c show a variety of different containers 200, 210, 220 each having a different predetermined configuration. As shown in FIGS. 2a–2c, the containers 200, 210, 220 have transducers 230, 240, 250 affixed at their bases respectively, so that the distance between the transducers 230, 240, 250 at the base of each of the containers 200, 210, 220 and the liquid-gas boundaries in each of the containers 200, 210, 220 corresponds to the height, h, of the liquid within each container. Thus, if the level or height, h, of the liquid within each of the containers 200, 210, 220 can be measured, a corresponding volume value can be determined.

For example, if the distance value, h, has been determined for the container 200 having a parabolic cross-section (FIG. 2a), then the volume of the liquid within the container 200 can be calculated as $V=Kh^2+C$, where K and C are constants which are determined by the exact dimensions of the container 200. K and C can be calculated using conventional calculus techniques for determining the volume of a solid configured so that its boundaries conform to a known mathematical equation. In the case of the container 210, having a cylindrical configuration (FIG. 2b), the volume of the liquid within the container can be calculated as $V=Ah$ where A is the cross-sectional area of the inside of the base of the container 210. Likewise, if the container 220 having a conical configuration (FIG. 2c) is employed, the volume of the liquid within the container 220 at a height h is calculated as $V=Kh^3+C$ where K and C are once again determined by the exact dimensions of the container 220. Similarly, the volume of liquid within any number of containers having a known configuration can be determined. Therefore, having obtained the level or height of a liquid in a container of a known configuration and dimension, we can also obtain the volume of liquid that a particular liquid level equates to.

Referring to FIG. 1, if the configuration of the container 120 is such that the increase in height (or depth) of the liquid 130 is consistent with an increase in volume as in the configurations described above, then it is a simple matter of converting each unit of liquid height to volume mathematically. However, many containers are not uniform in configuration, and therefore the height-to-volume conversion is not constant. For example, FIGS. 3a–3c illustrate irregularly shaped containers which can be used in accordance with the present invention.

Figure 3A:
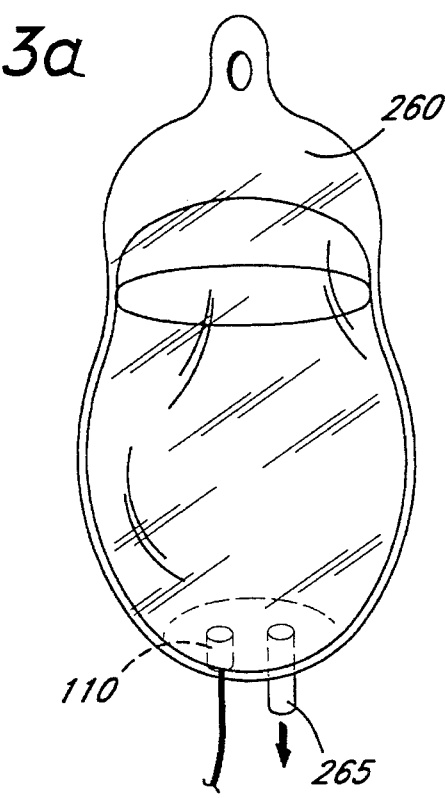
FIGS. 3a–3c show three different irregular container configurations.
Figure 3B:
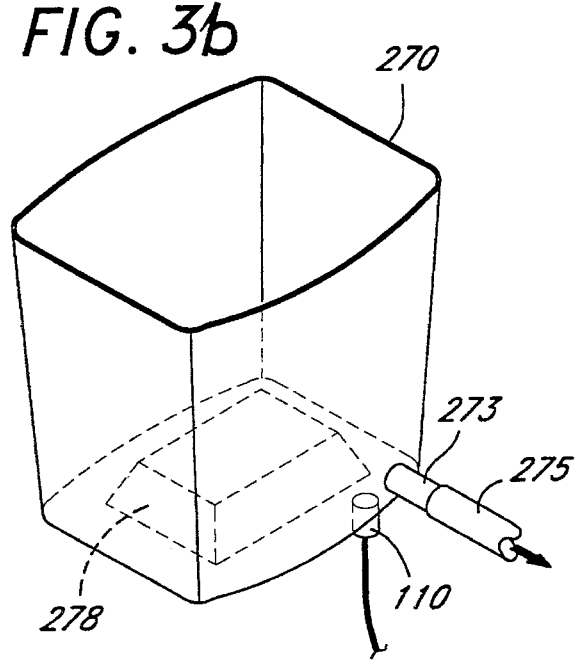
Figure 3C:
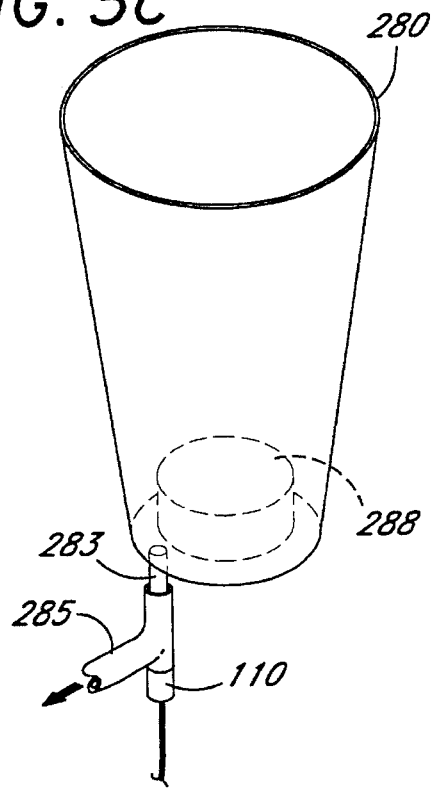

FIG. 3a shows a flexible container 260 (e.g., an IV gravity drip bag) wherein the height of the liquid within the container holds a varying relation to the volume of the liquid within the container. The container 260 includes a liquid outlet tube 265 at its base, and has the transducer 110 affixed proximate to the liquid outlet tube 265. FIGS. 3b and 3c show irregularly shaped containers 270, 280 having configurations which are not readily described mathematically.

The container 270 includes an outlet port 273 on the side of the container 270 at substantially the lowest point of the container 270. The outlet port 273 is in fluid connection with a liquid outlet tube 275 which allows liquid to drain from the container 270. The transducer 110 is affixed to the container 270 proximate to the port 273 so that the transducer 110 is also at substantially the lowest point of the container 270.

Also included within the container 270 is a liquid volume displacer 278. The liquid displacer 278 displaces liquid at the bottom of the container 270 so that the height to volume ratio is increased at the lower portion of the container 270 when the volume of the liquid is low. By increasing the height to volume ratio at the bottom of the container, higher resolution measurements of the liquid level can be made when the volume of the liquid is low.

Referring to FIG. 3c, the container 280 includes an outlet port 283 on the base of the container 280 at substantially the lowest point of the container 280. In the embodiment shown, the outlet port 283 is in fluid connection with a Y-shaped outlet tube 285. The Y-shaped outlet tube 285 has one branch which allows liquid to flow out from the container 280, and another branch which is adapted to receive the transducer 110 so that the transducer 110 is situated directly below the port 283. The container 280 also includes a liquid volume displacer 288 which serves substantially the same purpose as the liquid displacer 278 within the container 270. Due to their irregular configurations, the containers 260, 270, 280 preferably have the correlation of liquid level to liquid volume determined empirically. The control and processing circuitry 150 associated with this volume sensor 100 will incorporate a "look-up" table, which allows the correlation of height (liquid level) to volume to be calculated for irregularly shaped containers 120.

Referring again to FIG. 1, in order to determine the volume of irregularly shaped containers as a function of the determined distance value, a calibration procedure is employed in accordance with one aspect of the invention. When it is desired to implement a new container 120 having an irregular configuration, the transducer 110 is placed in sonic connection with the container 120 by means of the adaptor 125. The user can then manually input information, by means of the keyboard and display 155, which will allow the process and control circuitry 150 to identify the irregularly configured container 120. In one embodiment, the circuitry 150 is able to identify the configuration of the container 120 by means of the adaptor 125. This can be done if it is expected that a container having the same configuration (and consequently the same adaptor) will be used in the future.

Once information identifying the new configuration has been stored within the system 100 memory, the container 120 is completely filled with a known volume of the liquid 130. A test pulse is then generated by the transducer 110, and the duration between transmission and reception of the test pulse is measured. The measured duration value is then stored within the memory of the process and control circuitry 150 in association with a value indicating the known volume of the liquid 130. Thus, the measured duration value can serve as an address value which is used to "look-up" the volume to which the measured duration corresponds.

The level of the liquid 130 within the container 120 is then decreased in small, known increments (e.g., volume increments of 5 milliliters), and the above procedure is repeated after each decrease in volume. Thus, a "look-up" table is formed having incremental duration values corresponding to each increment in volume. During actual operation of the volume sensor system 100, certain duration values will be measured which may not correspond exactly with the incremental duration values obtained. Those measured duration values which do not exactly correspond to the stored incremental duration values can be interpolated, or rounded to the nearest stored duration value, depending upon desired precision. In this way each duration value is associated with a known volume value so that the volume of the liquid 130 within the irregularly shaped container 120 can be determined for a given duration value.

Of course, the parameters of the system 100 can be changed depending upon operating considerations such as the accuracy of volume measurement desired. For example, in order to obtain more accurate volume measurements, the volume increments used in accordance with the above described calibration procedure can be decreased to 1 milliliter or less. Furthermore, it is possible to begin with the container 120 empty and increase the volume of the liquid 130 in known volume increments to create the desired "look-up" table.

It should be noted that when the container 120 approaches empty, or the volume of the liquid 130 is very small, the duration time between the transmission and reception of the ultrasonic pulses 160, 162 becomes very short. If the duration time becomes too short this could cause problems with signal interference between pulses. Namely, the reflected "echo" pulse 162 could return to the transducer 110 before transmission of the pulse 160 is complete. In addition, a shorter duration time can also decrease the accuracy of the system.

In order to prevent signal interference and retain accuracy of measurement for very small volume levels of the liquid 130 within the container 120, it may be necessary to incorporate certain features into the system 100 which provide for an increased signal duration time. FIGS. 4a and 4b show two alternative embodiments of the system 100 which provide for a longer duration time.

FIG. 4a is a cross-sectional view of a container 300, which holds a small volume of the liquid 130, and includes an extended well 310 at its base. The well 310 is open to the container 300 so that the liquid 130 is able to flow into the well 310. The transducer 110 is affixed to the bottom of the well 310 by means of an adaptor 320, so that the transducer 110 is in sufficient sonic communication with the well 310 to transmit an ultrasonic pulse through the liquid 130 within the well 310. An outlet valve 330 is situated at the base of the container 300, above the bottom of the well 310, so that the liquid 130 within the well 310 is not considered when determining the volume of the liquid 130 within the container 300. This is because, in normal operation, the liquid 130 within the well 310 does not flow out of the container 300, but remains within the well 310, so that it is not useable liquid. Thus, the container 300 is effectively empty when the only liquid 130 present is that which is within the well 310.

When it is desired to determine the volume of the liquid 130 within the container 300, the same general procedure described above with reference to FIG. 1 is employed, except that the height of the liquid 130 is calculated to take account of the height of the liquid 130 within the well 310. Namely, the height of the liquid 130 within the container 300 is determined by measuring the time between the transmission and reception of the pulses 160,162, converting the measured duration into distance, and then subtracting a distance equal to the length of the well 310. Because the height of the liquid 130 in the well 310 is subtracted out when the effective height of the liquid 130 within the container 300 is determined, the system 100 will indicate that the container 300 is empty when the liquid 130 in the well 310 is the only liquid present. In a preferred embodiment, the well 310 is long enough so that the ultrasonic pulses 160, 162 are able to propagate without interference. That is, the length of the well 310 should be such that the time required for an ultrasonic pulse to propagate through twice the length of the well 310 is greater than the dwell time of the pulse 160. Thus, even if the container 300 is approaching "empty," sufficient time will be provided for the pulses 160, 162 to be transmitted and received by the transducer 110 without interference so that accurate remaining volume data can be obtained.

FIG. 4b shows a cross-sectional view of a container 350 which holds a small volume of the liquid 130, and includes an ultrasonically permeable extension 360 at its base. The transducer 110 is affixed to the bottom of the extension 360 by means of an adaptor 370, so that the transducer 110 is in sufficient sonic communication with the ultrasonically permeable extension 360 to transmit an ultrasonic pulse through the extension 360 to the liquid 130 within the container 350. Of course, the extension 360 can be affixed to or integrally formed with the transducer 110 or the container 350. An outlet port 380 is situated at the base of the container 350. The extension 360 can be made of a number of ultrasonically permeable materials which do not significantly dampen ultrasonic pulses, such as ceramic, plastics, or the like.

The extension 360 serves essentially the same purpose as the well 310 in FIG. 4a. That is, the extension 360 provides a sufficient distance through which the pulses 160, 162 can propagate so that, when the container 350 is empty, enough time is provided for the pulses 160, 162 to propagate without interference. Accordingly, the extension 360 should be of such a length and material that the time it takes for an ultrasonic pulse to propagate through twice the length of the extension 360 is greater than the dwell time of the pulse 160. Thus, in the embodiment described in FIG. 4b, sufficient time will be provided for the pulses 160, 162 to be transmitted and received by the transducer 110 without interference when the container 350 is empty. One advantage of the solid extension 360 over the liquid well embodiment is that essentially 100% of the liquid in the container is available for use.

Figure 5:
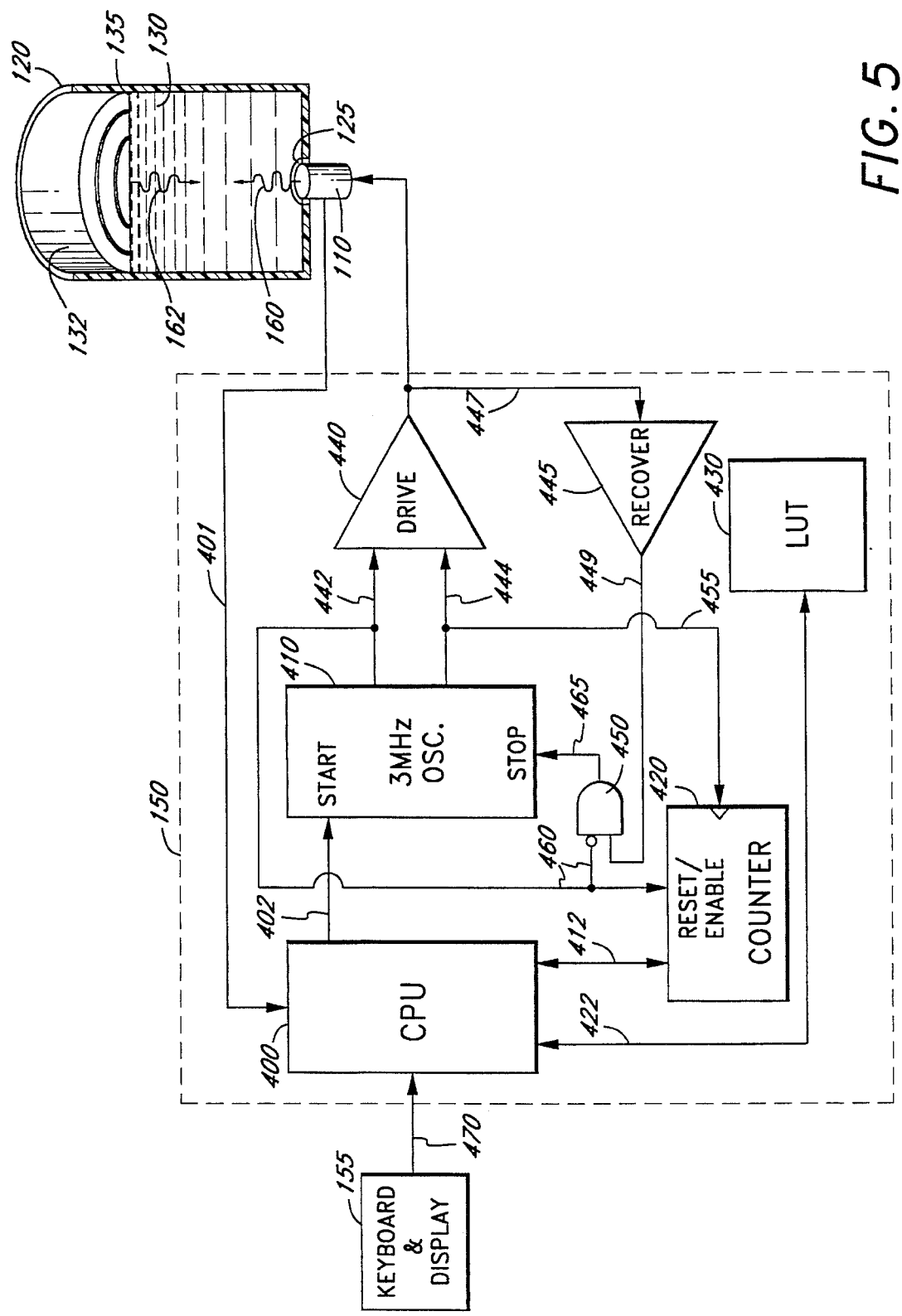
FIG. 5 is a schematic diagram showing the major components of the process and control circuitry.

FIG. 5 is a simplified block diagram which details the major functional elements of the process and control circuitry 150. The circuitry 150 includes a Central Processing Unit (CPU) 400 (e.g., Siemens 80C535 8-bit microprocessor), which is electrically connected to the transducer 110 via a line 401 and a 3 MHz oscillator 410 via a line 402. The CPU 400 is also electrically connected to a counter 420 via a bidirectional bus 412, and a look-up table memory (LUT) 430 via a bidirectional bus 422. The oscillator 410 is electrically connected to a drive amplifier 440 via an enable input line 442 and a signal input line 444. The output of the drive amplifier 440 is electrically connected to the transducer 110. The transducer 110, as well as the output of the drive amplifier 440, is electrically connected to a recover amplifier 445 via an input line 447. The output of the recover amplifier 445 is connected to a non-inverting input of an AND gate 450 via a line 449. The clock input of the counter 420 is connected to the line 444 via a line 455, and reset and enable inputs of the counter 420 are in electrical connection with the enable input line 442 via a line 460. The line 460 is also in electrical connection with an inverting input of the AND gate 450. The output of the AND gate 450 is connected to the disable input of the oscillator 410 via a line 465. Finally, the keyboard and display 155 is connected to the CPU 400 via a line 470.

The operation of the process and control circuitry 150 will be explained with reference to the block diagram of FIG. 5 and the timing diagrams of FIGS. 6a–6c. When it is desired to determine the volume of liquid 130 within the container 120, the above-described system calibration and initialization operations are performed after the transducer 110 has been connected to the container 120 by means of the adaptor 125. Once the transducer 110 is connected to the adaptor 125, a signal can be transmitted from the adaptor 125 to the CPU 400 via the transducer 110 and the line 401.

After the system 100 has been calibrated and initialized, the CPU 400 transmits a signal to the oscillator 410 along the line 402 which enables the oscillator 410. Once the oscillator 410 is enabled, the oscillator 410 outputs an amplifier enable signal 502 (FIG. 6a) in synchronization with a continuous 3 MHz input signal 506 (FIG. 6b) to the drive amplifier 440 across the lines 442, 444 respectively. The enable signal 502 enables the amplifier 440 so that a signal which is applied to the input line 444 will be amplified at the output of the amplifier 440. Thus, when the enable signal 502 is high (i.e., logically active), the input signal 506 is amplified at the output of the amplifier 440. In one embodiment, the enable pulse 502 has a duration of approximately 2 microseconds, and the input signal 506 on the line 444 is a 3 MHz square wave so that six cycles of the square wave 506 are passed and amplified by the driving amplifier 440. In addition to being applied to the drive amplifier 440, the enable signal 502 is applied across the line 460 to a start input of the counter 420, and the input signal 506 is applied across the line 455 to a clock input of the counter 420. Thus, after the enable signal 502 has gone low, the counter 420 will count the number of cycles of the signal 506 until the cessation of the signal 506.

The output of the amplifier 440 is shown as the electrical pulse 510 (FIG. 6c) which is applied to the line 447. This output pulse 510 is transmitted to the transducer 110 where the electrical pulse 510 causes the crystal within the transducer 110 to vibrate at the same frequency as the signal 510 (i.e., 3 MHz). The vibration of the crystal causes the ultrasonic pulse 160 to propagate through the liquid 130 as described above with reference to FIG. 1. When the reflected "echo" pulse 162 returns, the crystal once again is caused to vibrate and produces an electrical signal pulse 512 with the same frequency as the pulse 162 on the line 447 at the input of the recover amplifier 445. Thus, the time at which the electrical pulse 510 is generated is substantially simultaneous with the generation of the ultrasonic pulse 160, and the time at which the electrical pulse 512 is generated is substantially simultaneous with the reception of the ultrasonic pulse 162.

The electrical pulse 512 is amplified and transmitted across the line 449 to the non-inverting output of the AND gate 450. Since the other input to the AND gate 450 from the line 460 is inverting, the output of the AND gate 450 will be high only when the input from the line 449 is high and the input from the line 460 is low (i.e., a logical zero). Thus, because the signal on the line 460 is the same as the signal applied to the line 442 (i.e., the enable signal 502), the output of the AND gate 450 will be high only when the enable pulse 502 is low and the signal on the line 449 is high. However, as can be seen from FIG. 6c which shows the signals 510, 512 applied to the line 447, and, after amplification, the line 449, the enable signal 502 lasts for the entire duration of the first electrical pulse 510. Therefore, the output of the AND gate 450 will first achieve a high state when the electrical pulse 512, caused by the return pulse 162 sensed by the transducer 110, is applied to the line 447 and, subsequently, the line 449.

When the output of the AND gate 450 at the line 465 is high, the oscillator 410 discontinues the output of the signal 506 along the line 444. The oscillator 410 will not resume output of the input signal 506 along the line 444 until the CPU 400 transmits another start signal to the oscillator 410 along the line 402. As stated above, the counter 420 is clocked by the signal 506 so that each cycle of the signal 506 is counted by the counter 420. Moreover, when the oscillator 410 discontinues output of the signal 506, the counter 420 ceases counting. Thus, the counter 420 initiates counting at the leading edge of the enable pulse 502 and ceases counting at the first detection of a logical one at the output of the AND gate 450, that is, the counter 420 ceases counting at the first detection of the pulse 512. The number of cycles accounted for by the counter 420 is therefore the number of cycles which occur from the leading edge of the enable pulse 502 to the first detection of the signal 512 by the recover amplifier 445. However, it can be seen that the leading edge of the enable pulse 502 is synchronous with the leading edge of the first cycle of the signal 506, and, similarly the signal 510. Thus, the counter 420 accounts for the number of full cycles which occur between the leading edge of the signal 510 and the first detection of the signal 512.

Since the time between the leading edge of the signal 510 and the first detection of the electrical pulse 512 is approximately equal to the duration between the transmission and reception of the ultrasonic pulses 160, 162, the number of cycles accounted for by the counter 420 corresponds to the number of cycles generated between the transmission and reception of the ultrasonic pulses 160, 162. Thus, the total time between the generation and reception of the ultrasonic pulses 160, 162 can be calculated by multiplying the number of full cycles accounted for by the counter 420 by the period of the oscillator output. For example, if the oscillator 410 outputs a 3 MHz square wave having a period of 0.33 microseconds, and the total number of full cycles accounted for by the counter 420 is 1,000 cycles, then the time duration between the generation and reception of the pulses 160, 162 is approximately calculated as 0.33 milliseconds.

If the container 120 has an irregular configuration, then each obtained duration value will correspond to a volume value within the LUT 430. Thus, the obtained duration value is simply used to address the appropriate memory location within the LUT 430 so that the volume value stored within the addressed memory location is output to the display 155. This output volume data is updated regularly (e.g., every 50 ms) so that the user is provided with a continuous reading which indicates the volume of the liquid 130 within the irregularly shaped container 120.

If the container 120 has a known configuration, however, the duration value can be used to determine the height of the liquid 130. The height of the liquid 130 can then be used to calculate the volume of the liquid 130 within the container 120. Once the time duration between the generation and reception of the pulses 160, 162 is determined, this value can be stored as a digital value within the CPU 400 or a separate memory (not shown). The height of the liquid 130 within the container 120 can be determined by dividing the stored time value in half, to account for the distance to and from the liquid-gas boundary 135, and multiplying by the velocity value which was previously obtained during calibration of the system 100. The calculation of the height of the liquid 130 is advantageously done within the CPU 400. For example, if the stored time value is 0.33 milliseconds, and the velocity of propagation is calculated to be 3,000 feet per second, then the height of the liquid 130 within the container 120 is calculated to be ½', or 6". Once the height of the liquid 130 has been calculated, this value can be used to determine the volume of the liquid 130 within the container 120 having a known configuration. For example, if the container 120 is a cylinder having a base area of 100 square inches, then the total volume of the liquid 130 having a height of 6" within the container 120 is calculated to be 600 cubic inches.

Of course, the description of the circuitry 150 provided above is by no means restrictive. For example, the oscillator 410 can be implemented within the CPU 400. Also, the LUT 430 can be implemented as a programmable logic array (PLA), and the AND gate 450 can be implemented as a multiplexer or other device which provides a desired output in response to a given input. Furthermore, the circuitry 150 can also include a number of buffer circuits, biasing resistors, coupling capacitors, debouncing circuits, and the like to insure smooth operation of the circuitry 150 at high frequencies. In addition, conventional circuitry to interface with the keyboard and display 155, peripherals such as a printer or a host computer, and the adaptor 125 can also be included within the circuitry 150.

The accompanying Appendix A is a detailed schematic diagram which is readily understood by one skilled in the art, and which shows each of the structural elements of the circuitry 150 in one preferred embodiment of the invention. Appendix A is hereby incorporated by reference.

II. Peripheral Devices Used with Fluid Volume Sensors

In a particularly preferred embodiment, the electronic circuitry 150 of the fluid volume sensor system of the present invention will allow for the control of a number of different peripheral devices and will provide functions besides the determination of the volume of a liquid in a container. Peripheral devices which can be used in conjunction with the present fluid volume sensor system include audible and visual alarms, for alerting a user to the presence of a predetermined volume of liquid in a container; pumps, to permit the filling and/or draining of a container; valves or restrictors that allow for the control of the flow of liquid into or out of a container; and a printer or other display means, for providing a readout of the volume measurements of the fluid level sensor system 100. Such peripheral devices will advantageously be controlled by the CPU 400 or by a peripheral host computer, so that the user can manually set, control, and monitor the parameters of the volume sensor system 100.

Any of a number of alarms, pumps, valves, and other peripheral devices can be controlled by and/or used with the fluid volume sensor system of the present invention. For example, audible alarms using speakers or solid state technology can be used. Visual alarms such as flashing LED, LCD, or incandescent lamp displays can also be used in addition to or instead of such audible alarms. Moreover, a number of different kinds of pumps can be used in this system. Preferably, a pump used with the present system provides for a means to control the pump externally through the use of another controller instead of or in addition to the pump's own controlling electronics. When the fluid volume sensor system is being used in a medical application, for example, infusion pumps such as the IMED 980C or IVAC infusion pumps can be used.

Furthermore, any of a number of valves known to those of skill in the art can be employed in the present system. Solenoid valves have been found to be particularly useful in medical applications of the fluid volume sensor system. Solenoid pinch valves, for example, can be actuated by the electronic circuitry 150 of the fluid volume sensor system in order to stop the flow of a liquid into or out of a container to which the fluid volume sensor system is connected. In some applications, it is anticipated that shape memory metals such as FLEXINOL can also be advantageously used. Such shape memory metals can, like conventional valves, act to pinch off tubing to occlude liquid flow associated with a container to which the fluid volume sensor system is connected.

The peripheral devices and electronic circuitry described above can, of course, be used to calculate, display, and/or control the volume or flow of any of a number of different liquids through containers which are outfitted with one or more fluid volume sensors. It is anticipated that fluid volume sensors can be particularly advantageously used to calculate and control the volume and/or flow of liquids whose volume and/or flow rate must be calculated and controlled with a degree of precision, such as liquids used in the therapeutic treatment of a mammal, such as a human. Such liquids can include, for example, blood and liquids containing medicines. Thus, the input or output of blood, urine, lymph, or a therapeutic liquid can be calculated and controlled with the fluid volume sensor system and with appropriate peripheral devices under the control of the electronic circuitry of the fluid volume sensor system. However, controlling the flow rate and/or volume of a non-medical liquid in a container, such as the flow of water into a hot tub or bath tub, can also be accomplished by the present system.

In one particular application, the electronic circuitry 150 of the fluid volume sensor system 100 will allow for the calculation of the amount of a liquid 130 which flows into or out of the container 120 over a specified period of time. This system will also allow for the calculation of the total change in volume of the liquid in the container over that period of time. To determine the amount of liquid which has flowed into a container over a specified period of time, the system operator is first required to input into the system's electronic circuitry 150 the output flow rate of the liquid 130. Advantageously, the output flow rate is inputted automatically by a pump which is electrically connected to the fluid volume sensor system 100. The output flow rate can be, for example, the infusion rate of the liquid 130 into a patient's bloodstream. The system 100 then calculates the change in the volume of the liquid 130 in the container 120 over a specified time interval. After multiplying the length of that specified time interval by the output flow rate to determine the volume of liquid which has flowed out of the container 120 (e.g., infused into a patient's body), the change in the volume of the liquid 130 in the container 120 is added to the volume of liquid which has flowed out of the container 120 to determine the amount of the liquid 130 which entered the container 120 during the specified period of time.

Likewise, the amount of liquid which has flowed out of a container can be determined by first inputting into the system's electronic circuitry 150 the input flow rate of the liquid 130. The system 100 then calculates the change in the volume of the liquid 130 in the container 120 over a specified time interval. After multiplying the length of that specified time interval by the input flow rate to determine the volume of liquid which has flowed into the container 120, the change in the volume of the liquid 130 in the container 120 is added to the input flow rate to determine the amount of the liquid 130 which left the container 120 during the specified period of time.

Figure 8:
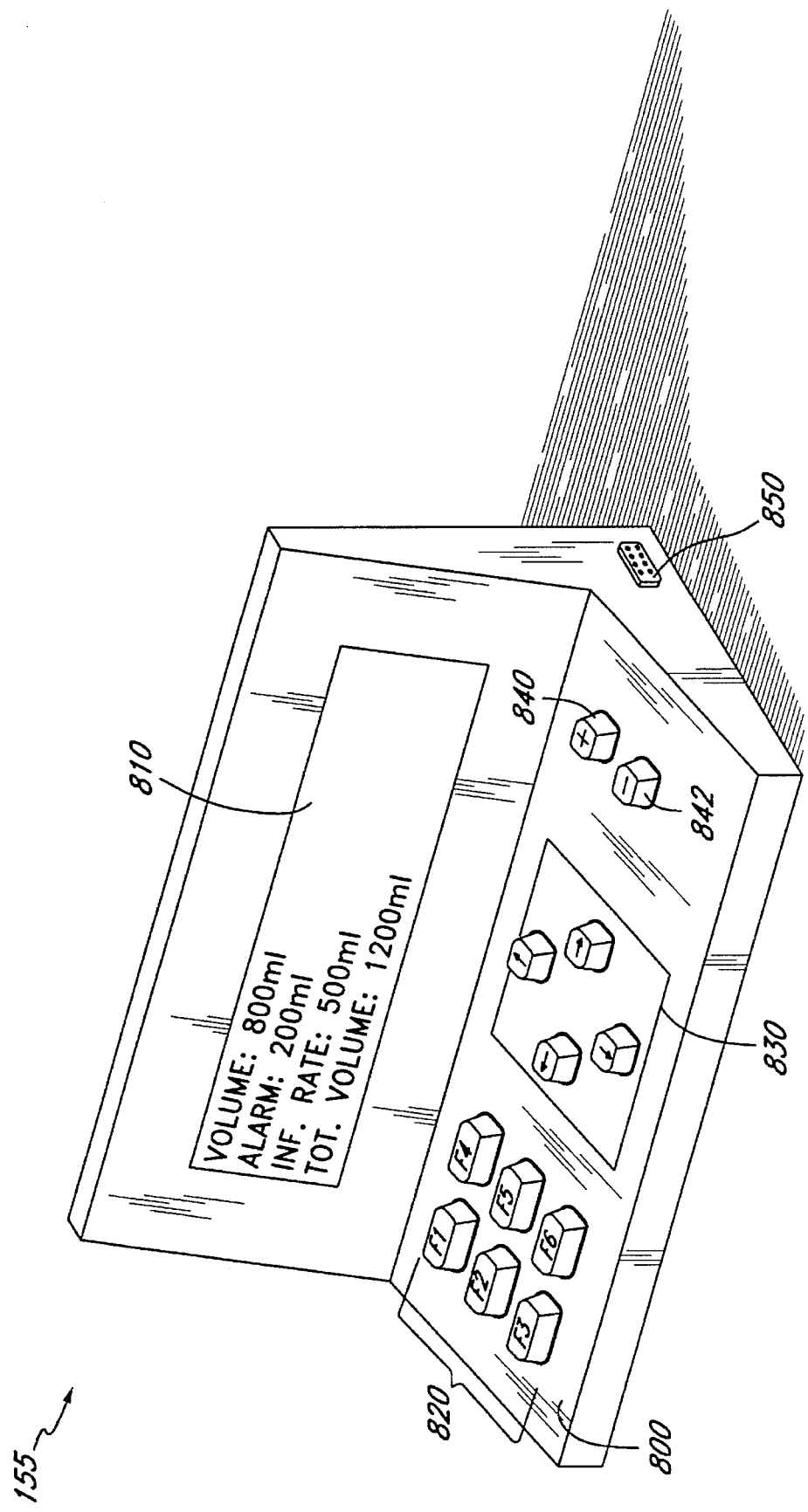
FIG. 8 is a perspective view of the keyboard and display user interface.

FIG. 8 is a perspective view which shows one embodiment of the keyboard and display user interface 155. The user interface 155 includes a keyboard 800, an LCD screen 810 and a printer connection port 815. The LCD screen 810 can be used to display such parameters as the volume of the liquid 130 within the container 120, the change in the volume of that liquid 130 over a period of time, the volume of liquid 130 which has flowed into or out of the container 120 over a period of time, and the low volume alarm setting. In one embodiment, the LCD screen 810 is updated every 50 ms so that the volume of the liquid 130 can be constantly monitored. In a preferred embodiment, the keyboard and display user interface 155 is able to display the volume of the liquid 130 remaining in the container 120, the differential volume over a selected time interval (i.e., the difference between volumes at two different times), and the time since the system has been in operation.

A user can input data and control the fluid volume sensor system 100 by means of the keyboard 800. In the embodiment shown, the keyboard 800 includes a plurality of function keys 820, a cursor control pad 830, and a pair of increment/decrement keys 840, 842. The function keys 820 allow the user to perform selected system functions. For example, the function keys 820 can be used to initiate calibration of the system 100, set alarm limits, input the infusion rate, and output data to a printer by means of the printer connection port 815. In addition, the function keys 820 can be used to set the time differentials for the purposes of measuring total liquid volume or liquid flow rate, or to set time increments for the purposes of trend analysis.

The fluid volume sensor system 100 can further be programmed to alarm the operator if the fluid volume in the container rises to a predetermined level, thus indicating a medical emergency (i.e., a high rate of bleeding). In this embodiment, the clinician is advantageously able to set the level at which the volume sensor system 100 activates an alarm. Thus, if a lower total volume of bleeding would indicate a medical emergency in a particular patient, such as an infant, the clinician can adjust the level at which the alarm activates to a lower level.

If a user wants to set an alarm limit, for example, the user selects the appropriate function key 820. This causes an alarm limit display to appear on the LCD screen 810. The user then positions a cursor, using the cursor control pad 830, so that the cursor is directly underneath the alarm limit value it is desired to change. The alarm limit value can then be increased by depressing the increment key 840, or decreased by depressing the decrement key 842, the appropriate number of times. This method can also be used to adjust or reset any one of the controllable values displayed by the keyboard and display interface 155.

It should be noted that the fluid volume sensor system 100 can be expanded to accommodate a host computer or like equipment for expanding the processing capabilities of the system 100.

In a further embodiment of the present invention, the level sensor electronics are configured to allow the use of multiple transducers. These multiple transducers are set up in such a manner that they are activated individually for totally separate reservoirs. Thus, a first reservoir has a first transducer, a second reservoir has a second transducer, and son on as desired. The device then keeps track of the information (liquid level or volume activity) obtained from each transducer. This information is accessible for each reservoir independently from one another, and the electronics differentiate which information belongs to which transducer or reservoir. Each transducer reservoir can be given a number or nomenclature to identify it, which can be read either on the LCD display or on the printout. The infusion rate, alarms as well as pumps or valves, can be programmed independently for each transducer.

In a further modification, the electronics are configured so that the data from the multiple transducers are combined into one. This could be useful on containers with multiple compartments that fluidically communicate with each other. These containers have compartments whose volumes would be cumulative in terms of the maximum liquid capacity that the container holds. The electronics are configured to treat each compartment as an addition or extension of the other compartment.

For example, a reservoir can have four compartments, each with a volume capacity of 500 milliliters (0.5 liter). If three compartments had 500 milliliters of liquid in them, and the fourth compartment had 300 milliliters of liquid in it, the total volume detected by the electronics for that container would be 1800 milliliters. A status could be given by the device on each compartment individually or on the combined total volume of all four compartments (the reservoir as a whole). The infusion rate, alarms, pump and valves will be activated as though a single transducer was addressed for a single reservoir. The "programming" requirements for the foregoing types of set ups will be apparent to one skilled in the art.

Liquid handling devices embodying the present invention provide significant advantages over the prior art, particularly in certain preferred medical applications. For example, in one application, the volume detector of the present invention is utilized to monitor the volume of blood drained from the chest cavity following open heart surgery. Frequently, following certain types of chest and heart surgery, a patient will be provided with a drainage tube for draining the chest cavity for a period of time following surgery. The volume of blood which is drained from the chest, and the rate at which the blood is drained, provide important feedback to the physician concerning the progress and healing of a patient, or the potential necessity for the re-admittance of the patient into surgery. Blood which has been drained into a container, moreover, is in some instances preferably reinfused continuously back into the patient, thereby complicating assessment of the total volume of blood drained from the chest cavity and rate of drainage. Since the rate of drainage will vary, the rate of reinfusion is frequently adjusted to roughly correlate with the rate of drainage. Generally, the rates are approximately equivalent, and it is important that the reinfusion pump be disengaged before the blood reservoir is completely emptied. Advantageously, the fluid volume sensor system 100 can be configured to control an infusion pump so as to reinfuse blood into a patient at approximately the same rate that blood is draining from that patient.

The system of the present invention also represents a vast improvement over current methods of determining blood volume data. At the present time, a nurse or other attendant must manually chart "in's and out's", that is, the volume of liquid flowing into and out of a container, such as a container collecting and reinfusing blood from a patient. Such in's and out's are normally charted on an hourly or other elapsed time basis, depending upon the particular hospital's protocol. This charting maintains a log of the volume drained into a container (or other reservoir) and the volume infused out of the container. Unfortunately, information concerning the total volume drained can only be determined after certain calculations (described above), which must take into account the varying drainage rates and infusion rates. This can disadvantageously delay receipt of the volume data, which may be needed quickly in an emergency situation. In addition, the total volume drained over a given time interval may be medically significant, yet cumbersome to arrive at quickly under present methods.

The fluid volume sensor system overcomes these problems by allowing for the automatic calculation and charting of the inflow and outflow of a liquid, such as blood, into a container. For example, if the system 100 is used with an autotransfusion device, which recycles blood from a patient, an operator can tell if the patient's bleeding increases, because the rate at which blood from the patient flows into the container 120 will increase. This increase can be detected through the charting of the inflow of liquid, in this case blood, into the container.

This and other data which can be collected and charted by the fluid volume sensor system 100 can be displayed by display interface 155, and can also advantageously be printed out on an attached printer (not shown). For example, the display interface 155 or printer can display fluid drainage trends which can, for example, be measured over five minute increments. In an even more preferred embodiment, this data can be displayed in graphical form, such as in the form of a chart or bar graph. Thus, an operator can easily and accurately monitor the trends of the liquid 130 within the container 120 over long periods. As stated above, this application can be advantageous in fields relating to medicine where it is important to accurately monitor the trends in a patient's retention or draining of body fluids.

If the user utilizes an infusion pump that is connected to the electronic circuitry of the present system, all calculations of liquid inflow and outflow in a container can be performed automatically, because the fluid volume sensor system can make use of a built-in program that calculates the "in's and out's". This program can advantageously collect output flow rate information directly from an infusion pump which is electrically connected to the fluid volume sensor system. If, however, the user does not utilize an infusion pump that is connected to the electronic circuitry of the system, the user then simply inputs the infusion rate that is programmed on the external pump into the system. With this system, the user has instant access to information such as: (1) volume drained over time (E.g., 1, 5, 15, 30, and 60 minutes); (2) volume infused over time (E.g., 1, 5, 15, 30, and 60 minutes); and (3) total volume drained from the start of drainage (initial hook-up) to present.

The pumps used with the fluid volume sensor system of the present invention can be either integrally connected to the electronic circuitry of the system or can be an external pump with which the system is connected. An integral pump holds the advantage, of course, of being connected to the fluid volume sensor prior to use by an operator, thus saving time and eliminating the possibility of incorrect connection by the operator. However, the electronic circuitry of the fluid volume sensor can also be connected to external pumps. For example, the electronic circuitry 150 of the fluid volume sensor can be connected to the external control port (RS232) of an IMED 980C infusion pump. The volume of liquid pumped, the pumping rate, the volume of liquid in a container at which pumping should begin and end, and other parameters can all be controlled by the fluid volume sensor, and such parameters can be programmed either at the site of the fluid volume sensor or at a remote location, such as a central station in a hospital.

In accordance with the present invention, the fluid volume sensor system can also be configured so that it is not necessary for an attendant to turn on or off an infusion pump if the reservoir volume of a container becomes too high or too low. The system can electronically control a pump, and can be programmed such that it turns on an infusion pump when the volume in the reservoir has reached a sufficient level and turns off the infusion pump when the volume level is low. These 'set points' are programmable over virtually the entire volume of the container.

If an infusion pump is utilized that does not directly interact with the electronics of the unit, the 'set points' can be used to trigger the built-in alarms. Upon reaching the user programmed 'set points', the user will be alerted visually and/or audibly, therefore allowing them to react appropriately. Such alarms can also be utilized even if the infusion pump is under the control of a fluid volume sensor's electronics. The visual, audible, or other alarms can be activated either on site or at a central station, such as a nurses' station.

III. Containers Used with Fluid Volume Sensors

A. Containers Having Permanently Mounted Transducers

One problem which has been encountered in the use of ultrasonic transducers for detecting the volume and/or level of a liquid in a container is that the face of such ultrasonic transducers can become scratched, warped, or otherwise damaged as these transducers are connected to and disconnected from various containers. Damage to the face of a transducer can interfere with the functioning of that transducer as part of a volume or level sensing device, because the transducer face must make intimate contact with the surface of a container in order for it to function properly.

If warpage or other damage causes the face of a transducer to become uneven, a pocket of air may exist between the transducer face and the surface of a container when the two are brought into intimate contact. Because ultrasonic signals are reflected by gaseous interfaces, the presence of air between the transducer face and the surface of a container will cause an ultrasonic signal emitted by the transducer to be immediately reflected, thus causing the volume or level sensing device to register an erroneous result.

One solution to this problem is to place a deformable, resilient substance, such as latex, between the transducer face and the surface of a container. As the transducer face is pressed against the latex, the surface of the latex will deform and then conform to the surface of the transducer face. Any areas of unevenness on the surface of the transducer will thereby be "filled in" by the latex, so that an ultrasonic signal passing from the transducer, through the latex, and into the container will not encounter any gaseous interfaces before entering the container. Alternatively, a coupling gel such as glycerine or silicone oil can be used to fill in any unevenness which exists between the surface of a container and the face of an ultrasonic transducer.

The use of latex or coupling gels to restore functionality to a damaged transducer, however, does not solve the underlying problem of transducers becoming damaged through repeated handling as they are coupled and uncoupled with various containers. The use of latex or coupling gels is also inconvenient. Therefore, in another aspect of the present invention, containers are provided which have ultrasonic transducers that are permanently affixed to the lower end of a container.

By permanently attaching a transducer to the lower end of a container, an operator of the transducer/container no longer needs to handle the transducer. This eliminates the possibility of damage to the transducer face through mishandling by the end user. Moreover, by eliminating this source of damage to a transducer, the reliability of a volume or level sensing device with which the transducer is used is also increased. When a volume or level sensing device is being used in situations where accuracy can be critical, such as in a medical setting, the reliability of the device is of paramount importance.

In this aspect of the invention, a transducer must be affixed to a container such that the face of the transducer is in intimate contact with the container, i.e., so that there are no pockets of air or any other gas between the transducer face and the surface of the container. In order to detect the volume and/or level of liquid in a container, the transducer is normally placed in the lower end of the container. The transducer is then affixed to the lower end of the container such that the face of the transducer is at least roughly parallel to the surface of a liquid in the container when the container holds a liquid. Securing the transducer to the container can be effected in any of a number of ways known to the art, including mechanically attaching the transducer through an interference fit with a seat on the container or using an adhesive.

As used herein, the "lower end" of a container denotes a point at or near the lowest point in the container. In most applications it is desirable to be able to determine when a container reaches empty, i.e. contains no liquid, in which case the transducer should be positioned at the lowest point in the container in which liquid can be present. However, if it is not absolutely necessary that the point at which a container becomes empty be monitored, the transducer can be positioned at a higher point in the container. As those of skill in the art can surmise, the fluid volume sensor cannot monitor changes in the volume of a liquid when the surface of that liquid is below the face of the transducer and the transducer face is pointing upward, as in the present invention.

In a particularly preferred embodiment, the transducer is embedded in the container, i.e., the transducer and container form an integral unit. In this embodiment, the seat is preferably also an integral part of the container, and can consist simply of the space within the lower end of the container which encloses or partially encloses the transducer. The embedding or encasement of the transducer provides added protection to the transducer and also eliminates the additional step of affixing the transducer to the container. If the container is formed from a plastic material, for example, the transducer can be placed in a mold and the container can then be formed through injection molding. In this embodiment, the seat in which the transducer is placed is a part of the container itself. Any suitable plastic material can be used for the container, such as polycarbonate or acrylic.

In this embodiment, however, the formation of the container around the transducer must not employ excessive temperatures or pressures which would interfere with the functioning of the transducer. Thus, the use of certain materials may not be practicable. In order to shield the transducer from potential damage during the formation of the container, the transducer can also itself first be encased in a protective material, such as epoxy.

The container/transducer of this aspect of the present invention (not shown in the Figures) must also include a reversible connection which provides an electrical link between the transducer and the electronic circuitry of the fluid volume sensor system. As used herein, the term reversible connection denotes a mechanical, magnetic, or other physical connection which also creates an electrical connection between two elements, namely between the transducer and the electronic circuitry of the fluid volume sensor system. This term can also refer to the element or elements used to make such a connection.

The reversible connection in this aspect of the present invention can be made in any way known to those of skill in the art. For example, the connection can be in the form of a socket for a plug, such as a plug for a stereo audio component, which is formed in the seat of the container (or in the container itself) and which is itself in electrical connection with the transducer. In this embodiment, the fluid volume sensor system would communicate with the transducer by means of a wire ending in a plug which would be connected with the socket of the container. Alternatively, such a socket can be located outside of the container and linked to the transducer through a wire extending out of the container to the socket.

Other means of making a reversible physical connection between two elements are of course possible. In the most simple embodiment, an electrical connection can consist of two conductive wires linked to the transducer which extend to at least the outer surface of the container. In this embodiment, the container is preferably formed from a non-conductive material, such as plastic, so that the container itself acts to insulate these two wires. The point at which the wires meet the surface of the container or extend beyond it is preferably formed so as to mate with a component of the fluid volume sensor system and thereby make a reversible connection.

Examples of reversible connections which can be used in this embodiment of the present invention are illustrated in FIGS. 9A, 19, 20, and 21. In FIG. 9A, a reversible connection is made when a plug 1520 is mechanically threaded into a socket which is formed, in this case, in the seat 960 of an adaptor 900, thereby physically connecting the plug 1520 with the seat 960. The electrical link between the transducer 970 and the plug 1520 (which is itself linked to electronic processing and control circuitry of the fluid volume sensor system) is formed when transducer electrical contacts 1510 and 1512 are contacted with plug electrical contacts 1522 and 1524.

Figure 19:
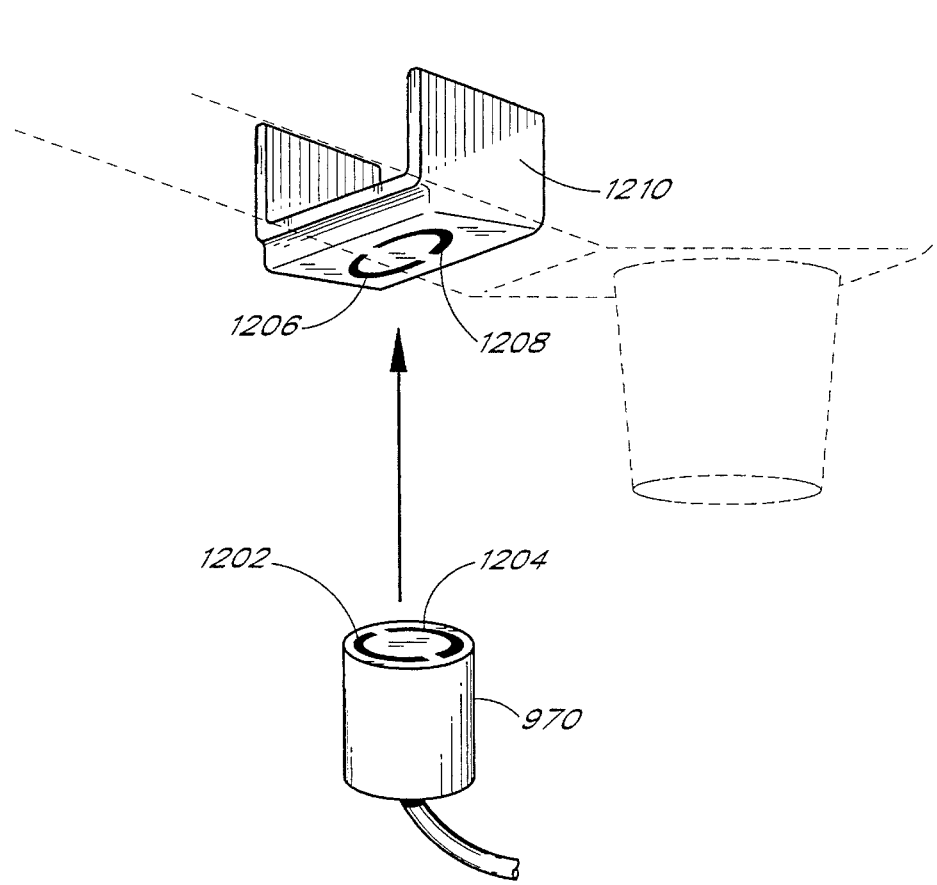
FIG. 19 is an isometric view showing an adaptor which can be attached to the bottom of a container (shown in phantom) and which uses a magnetic coupling to secure an ultrasonic transducer.
Figure 20:
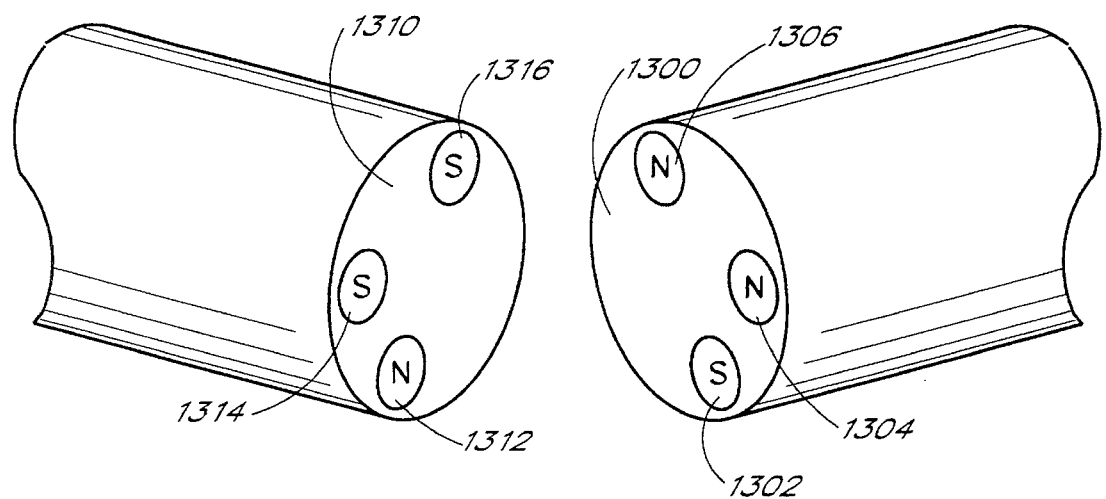
FIG. 20 is an isometric view of a magnetic coupling arrangement which can be used to secure an ultrasonic transducer to a seat in an adaptor of the present invention.
Figure 21:
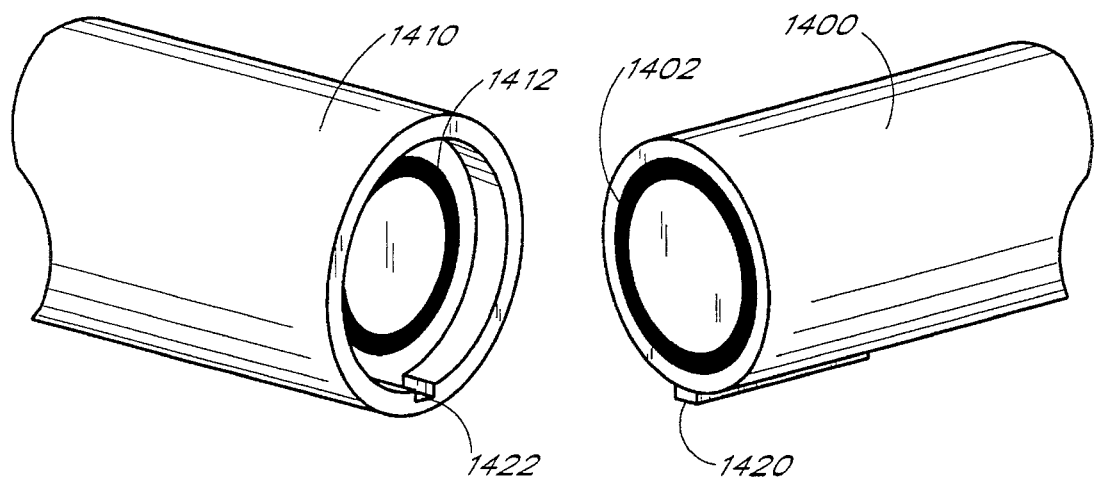
FIG. 21 is an isometric view of an alternate magnetic coupling arrangement which makes use of a key slot and which can be used to secure an ultrasonic transducer to a seat in an adaptor of the present invention.

A physical connection can also be made magnetically, as shown in FIGS. 19, 20, and 21. In FIG. 19, a physical connection is made between the transducer 970 and, in this case, the adaptor 1210 when magnetic materials 1202 and 1204 make magnetic contact with magnetic materials 1206 and 1208, respectively, which are of opposite polarity. Likewise, in FIG. 20, a physical connection is made when magnetic materials 1302, 1304, and 1306 make contact with magnetic materials 1312, 1314, and 1316, respectively. In FIG. 21, a magnetic connection is made between magnetic materials 1402 and 1412 (which are preferably of opposite polarity), and in addition element 1420 helps to laterally stabilize this connection when it is fitted into slot 1422.

B. Flexible and Semi-Rigid Containers

In another aspect of the present invention, flexible and semi-rigid containers are provided which are adapted to be used with an ultrasonic fluid level or volume sensor. Such containers are preferred in some situations to containers which are completely rigid, because a liquid can be drained from a flexible or semi-rigid container without the need for a vent to the atmosphere, thus keeping air from becoming entrained in the liquid. As used herein, the term "flexible container" refers to a container whose walls will deform outwardly under the pressure of a non-pressurized liquid placed in such a container. The walls of a flexible container can also deform inwardly when liquid is removed from such a container. The term "semi-rigid container" on the other hand refers to a container in which at least one wall is flexible, that is, it will deform under the pressure of a non-pressurized liquid placed in the container, and in which at least one wall will retain its shape when the container holds a non-pressurized liquid.

In order to be able to use an ultrasonic fluid level or volume sensor with a flexible or semi-rigid container, it is important that the container provide a signal path between the transducer of the fluid volume sensor and the surface of a liquid in the container when the container holds a liquid, so that an ultrasonic signal can be passed therethrough. This path must not be obstructed by a liquid-gas interface, because such an interface would cause an ultrasonic signal passing through the liquid phase to be reflected, thus interfering with the operation of the fluid volume sensor. A liquid-gas interface can occur in a flexible container, for example, if a side wall of the flexible container collapses into the path of an ultrasonic signal from a fluid volume sensor as the liquid drains out of the flexible container. The interface between the bag and the atmosphere would reflect the ultrasonic signal and interfere with the operation of the sensor.

As used herein, an ultrasonic signal path denotes the area through which an ultrasonic signal passes when it leaves a transducer. In the present fluid volume sensor system, such a signal path will extend generally upward from the seat for an ultrasonic transducer through the lower end of a container. This signal path will also be generally perpendicular to the surface of a liquid in a container so that an ultrasonic signal propagated therethrough will be reflected back to the transducer which generated it.

Figure 14:
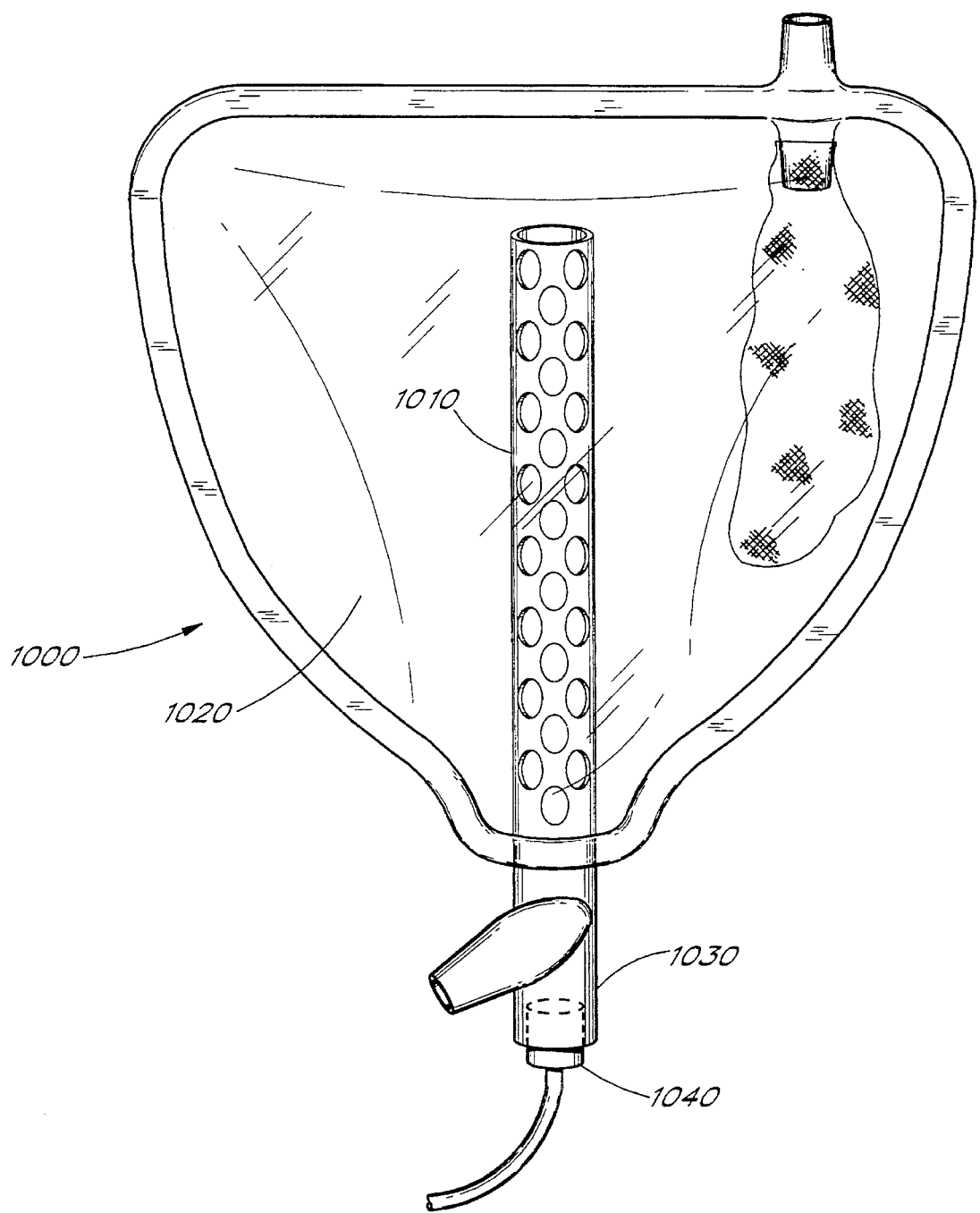
FIG. 14 depicts one embodiment of a flexible container for liquids adapted for use with an ultrasonic fluid volume sensor.
Figure 15:
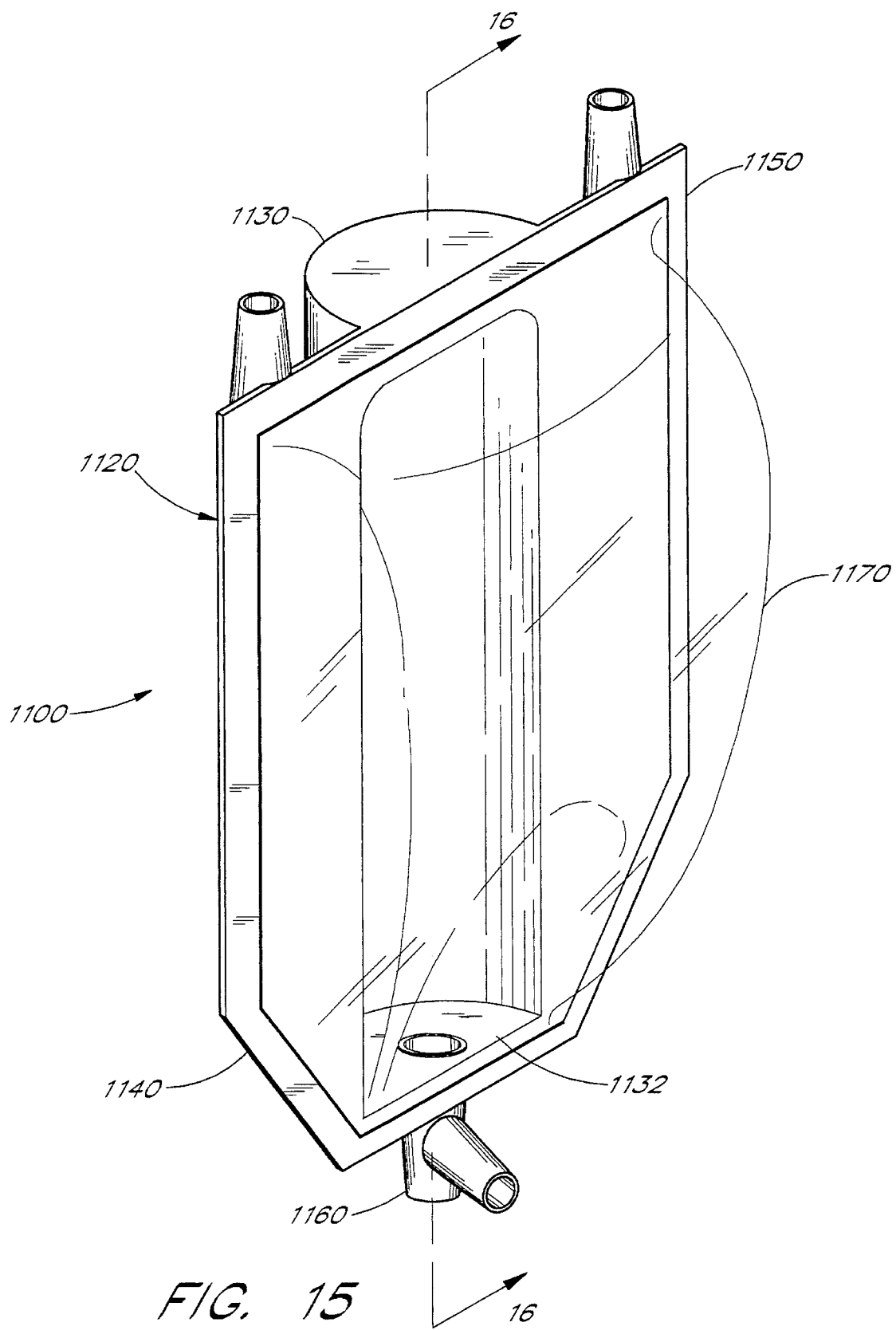
FIG. 15 depicts one embodiment of a semi-rigid container for liquids adapted for use with an ultrasonic fluid volume sensor.
Figure 17:
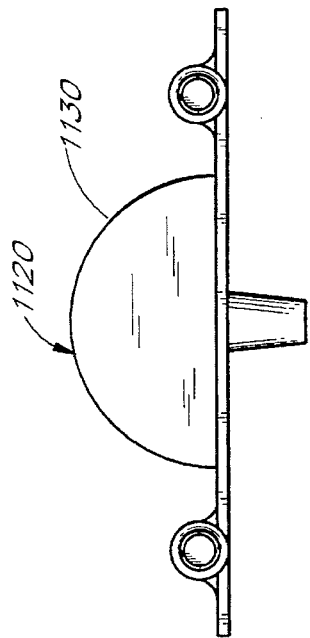
FIG. 17 is a top view of the semi-rigid container depicted in FIG. 15.
Figure 18:
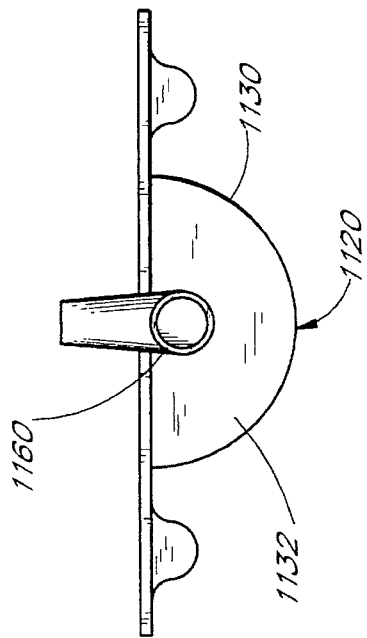
FIG. 18 is a bottom view of the semi-rigid container depicted in FIG. 15.
Figure 16:
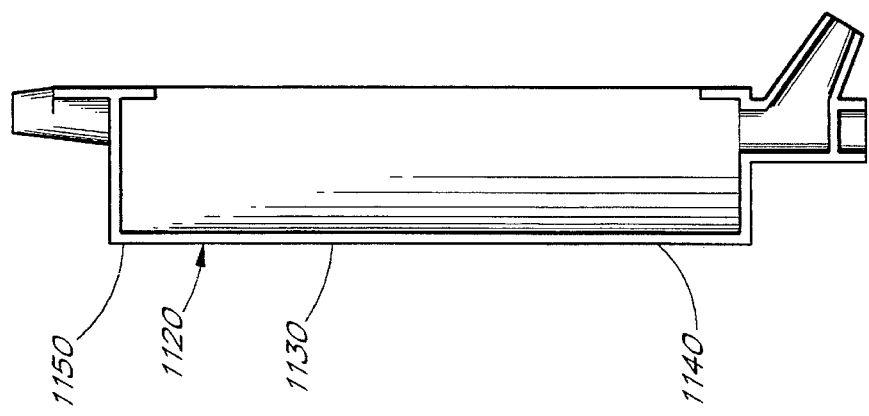
FIG. 16 is a cross-sectional view of the semi-rigid container depicted in FIG. 15 taken along line 16—16 of FIG. 15.

A flexible container therefore normally requires a structural framework or the like in order to prevent the collapse of the flexible wall or walls of such a container. FIG. 14 illustrates one embodiment of this aspect of the present invention, in which a rigid, cylindrical or tubular structure 1010 encompasses at least part of the signal path of an ultrasonic transducer 1040 inside a flexible container 1000. This tubular structure 1010 sits directly above a seat 1030 in the container 1000 for the ultrasonic transducer 1040.

The tubular structure can be made of any suitably rigid material, such as polycarbonate, PVC, or metal. Flexible containers 1000, such as blood bags or bags used to pass liquids into a patient through drip-infusion, are typically made from PVC. When the container 1000 is used in the medical field, the materials used to form the container 1000 and tubular structure 1010 must, of course, be compatible with the biological liquids passing therethrough, i.e. they must not dissolve through contact with such liquids and must be non-toxic. Preferably, the container 1000 and tubular structure 1010 are also clear when used in the medical setting, so that the passage of liquids or other matter through the container 1000 can be observed. For reasons of hygiene, it is preferred that plastic materials be used for the container 1000 and tubular structure 1010 in medical settings, because such materials are inexpensive and can be disposed of easily.

Preferably, the wall of the tubular structure 1010 contains holes or slots which allow a liquid in the container 1000 to enter and exit the tubular structure 1010. In this way, as the level and volume of a liquid in a flexible container changes, the level of the liquid which is within the tubular structure 1010 will equilibrate with the liquid level outside the tubular structure 1010. The tubular structure 1010 can alternatively comprise a screen or other open weave structure that allows liquids to pass through the tubular structure easily, as long as such a structure is sufficiently rigid to prevent the walls of the container 1000 from collapsing over the signal path within the tubular structure 1010.

Although a cylindrically-shaped structure 1010 is depicted in FIG. 14, the shape of this structure is not believed to be critical to the functioning of the container 1000. Other non-tubular frameworks that prevent the collapse of the container's walls 1020 across the transducer's ultrasonic signal path, such as a rectangular or elliptical framework (not shown in the Figures), can also be used. Alternatively, a rigid framework (also not shown in the Figures) can be attached to the outside surface of the walls 1020 of the container 1000 to prevent such collapse.

Semi-rigid containers can also be adapted for use with an ultrasonic fluid volume sensor. In one embodiment (not shown in the Figures), a semi-rigid container can contain a tubular structure such as that depicted in FIG. 14 in order to prevent the collapse of a flexible wall into the signal path of an ultrasonic signal being propagated in the semi-rigid container. Alternatively, one or more rigid walls of a semi-rigid container can be fashioned so as to prevent the collapse of one or more flexible walls of the semi-rigid container. For example, in the embodiment of the present invention depicted in FIGS. 15–18, a recessed area 1130 in a rigid, otherwise flat wall 1120 of a semi-rigid container 1100 which extends from a lower end 1140 of the container 1100 to an upper end 1150 can serve to protect an ultrasonic signal path. In this embodiment, an ultrasonic transducer of a fluid volume or level sensing device can be attached to a floor 1132 of the recessed area 1130, or can alternatively be placed in a seat (not shown in the Figures) in the outlet 1160 of the container 1100.

The rigidity of the rigid wall 1120 and the recession of the recessed area 1130 will prevent the flexible wall 1170 of the container 1100 from collapsing in onto an ultrasonic signal path within the recessed area 1130 as liquid empties out of the container 1100. Other means of preventing such collapse which take advantage of the rigidity of the rigid wall 1120 can also be used, however. For example, ribs having slots or holes to allow the passage of a liquid therethrough and which project axially from the rigid wall 1120 (not shown in the Figures) can be used to encompass and protect an ultrasonic signal path in the bag.

The rigid wall 1120 of the semi-rigid container 1100 can be made from any suitably rigid material, such as polycarbonate, acrylic, or polystyrene. The flexible wall or walls 1170 of such a container, like the flexible walls of the container depicted in FIG. 14, can be made from suitably flexible materials such as PVC, as described above. Considerations of cost, rigidity, clarity, and hygiene will determine the best material to be used in a particular application, as is known to those of skill in the art and as is discussed above.

If a seat or other convenient area is not provided in a flexible or semi-rigid container for the attachment of an ultrasonic transducer of an fluid volume or level sensing device, such a transducer can, of course, be attached to the outlet port of the container through an adaptor 900 of the present invention.

IV. Adaptors for Fluid Volume Sensors

A. Adaptors for Specific Containers

As has been discussed above, the fluid volume sensor system of the present invention can be used to determine the volume of any of a number of fluids in a wide variety of different containers. Due to the numerous configurations of containers with which the fluid volume sensor system 100 can be used, the electronic circuitry of the fluid volume sensor system 100 is preferably able to display on command a menu of containers from which the user can select. This can be done, for example, by means of the keyboard and display 155.

Figure 19A:
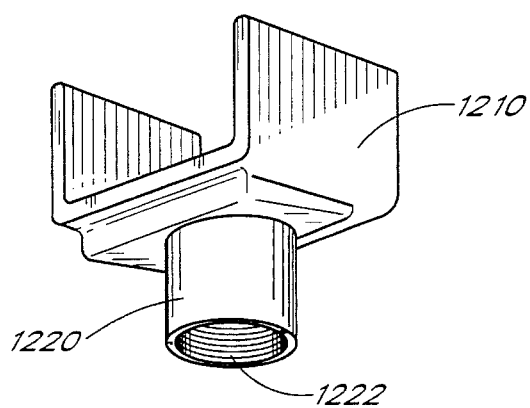
FIG. 19A is an alternate embodiment of the adaptor of FIG. 19.

Another means for ensuring that the fluid volume sensor of the present invention is correctly calibrated for use with a particular container is to provide an adaptor which is uniquely adapted to fit onto that container. In other words, in this embodiment of the present invention the adaptor into which the transducer is to be installed must be one that was specifically designed for that unique container. One example of such an adaptor is shown in FIG. 19. In this embodiment, the adaptor 1210 resembles a saddle and fits astride the bottom of a container (shown in shadow). An alternative embodiment of the adaptor 1210 is shown in FIG. 19A. In this alternative embodiment, the transducer (not shown) is mechanically attached to the adaptor 1210 by means of threads 1222 in a transducer housing 1220 which would engage grooves on the transducer.

Preferably, if the adaptor does not match that container, the circuitry 150 will not allow the system 100 to be used. This sequence of events is desirable to make sure that the correct "look-up table" is selected by the circuitry 150. The circuitry will allow for a desired number of different "look-up" tables by programming a programmable chip or chips. This then will accommodate any new container configurations with which the system can be used by simply adding them in. A detailed description of further specific adaptor configurations which can be used in accordance with the present invention is given with reference to FIGS. 7a and 7b below.

The adaptor 125 advantageously includes an indicator which can be used to identify the configuration of the container 120. For example, the adaptor 125 can include a bar code label on the surface where the transducer 110 is to be affixed. An optical arrangement, such as a photo-diode sensing device can then be incorporated into the transducer 110 as an accessory so that the photo-diode is capable of reading the bar code. The bar code advantageously includes information which can be used to identify the specific adaptor 125 so that the configuration of the container 120 is recognized by the processing circuitry 150.

When an indicator signal is transmitted from the adaptor 125 to the CPU 400 (via the transducer 110 and the line 401), the CPU 400 initiates a pre-programmed response by which it automatically identifies the configuration of the container 120 to which the adaptor 125 is affixed. If the configuration of the container 120 is not one which is recognizable by the system circuitry 150, then the user can input the dimensions and configuration of the container 120 manually, or a calibration procedure can be performed to install the new configuration.

Figure 7A:
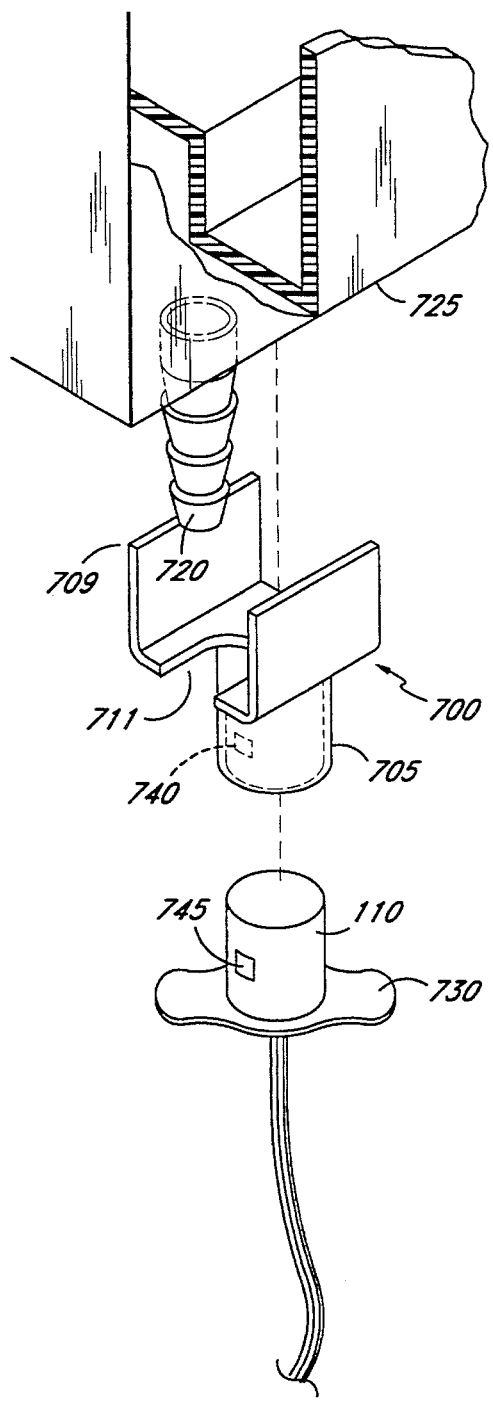
FIGS. 7a and 7b are exploded assembly views which show possible embodiments of the transducer adaptor.

In one embodiment, shown in FIG. 7a, an adaptor 700 is made of a durable plastic, and includes a receiving member 705 which can be cylindrical or other configuration, and a connecting saddle 709. The saddle 709 has a locator notch 711 which is constructed to receive an outlet port 720 of a container 725. By situating the adaptor 700 so that the saddle 709 embraces the base of the container 725, and the notch 711 fits snugly about the outlet port 720, the adaptor 700 is effectively located proximate to the lowest point on the container 725. This is because the outlet port 720 is typically located at the lowest point of the container 725.

The cylinder 705 is constructed to receive the transducer 110 so that the transducer 110 is held firmly within the adaptor 700. Gripping members 730 are advantageously provided at the base of the transducer 110 so that a user can conveniently insert and remove the transducer 110. The adaptor 700 is also provided in some embodiments with a bar code 740 (shown in phantom) which is located on the inside surface of the cylinder 705. The transducer 110 is constructed to include a sensing photo-diode 745, which is positioned so that it coincides with the bar code 740 when the transducer 110 is secured within the adaptor 700. The photo-diode 745 is therefore capable of sensing the bar code 740 and transmitting a signal to the CPU 400 via the line 401 (FIG. 5). The signal which is transmitted to the CPU 400 indicates the model of the adaptor 700. Since the adaptor is uniquely configured to be mountable only to a specific container, this information is then used to determine the type of container 725 which is to be employed.

The embodiment of the adaptor shown in FIG. 19 illustrates a means for assuring the connection of the correct transducer with a specific adaptor which makes use of a magnetic material (i.e., a material which attracts metals and other magnetic materials of opposite polarity). Specifically, magnets 1202 and 1204 of opposite polarity align with magnets 1206 and 1208, also of opposite polarity. Although no indicator signal is transmitted in this embodiment, the unique configuration of magnets on the saddle 1210 and on the transducer 970 assure that the transducer 970 can be securely attached only to the saddle 1210. The magnets 1202, 1204, 1206, and 1208 thus provide the dual functions of assuring transducer specificity and providing a magnetic coupling.

FIGS. 20 and 21 provide further embodiments of adaptors which make use of magnetic materials. In FIG. 20, element 1300 (which could be either a transducer or an adaptor or other seat for a transducer) will be magnetically (and ultrasonically) connected to element 1310 when magnetic materials 1302, 1304, and 1306 align and come into contact with magnetic materials 1312, 1314, and 1316, respectively. Since the magnetic materials 1302, 1304, and 1306 can only magnetically and ultrasonically connect elements 1300 and 1310 when they are in the foregoing mirror-image alignment with magnetic materials 1312, 1314, and 1316, this alignment serves the dual purpose of magnetic coupling and transducer specificity.

In the embodiment shown in FIG. 21, the transducer 1400 is also coupled to a seat 1410 by means of a magnetic coupling between magnetic material 1402 and magnetic material of opposite polarity 1412. Transducer specificity, however, is assured instead by mechanical means, namely the use of key element 1420 and keyhole slot 1422. Of course, other combinations of mechanical, magnetic, and other means of coupling a transducer and a container or adaptor can also be employed, as one of skill in the art will know based on the present disclosure.

Figure 7B:
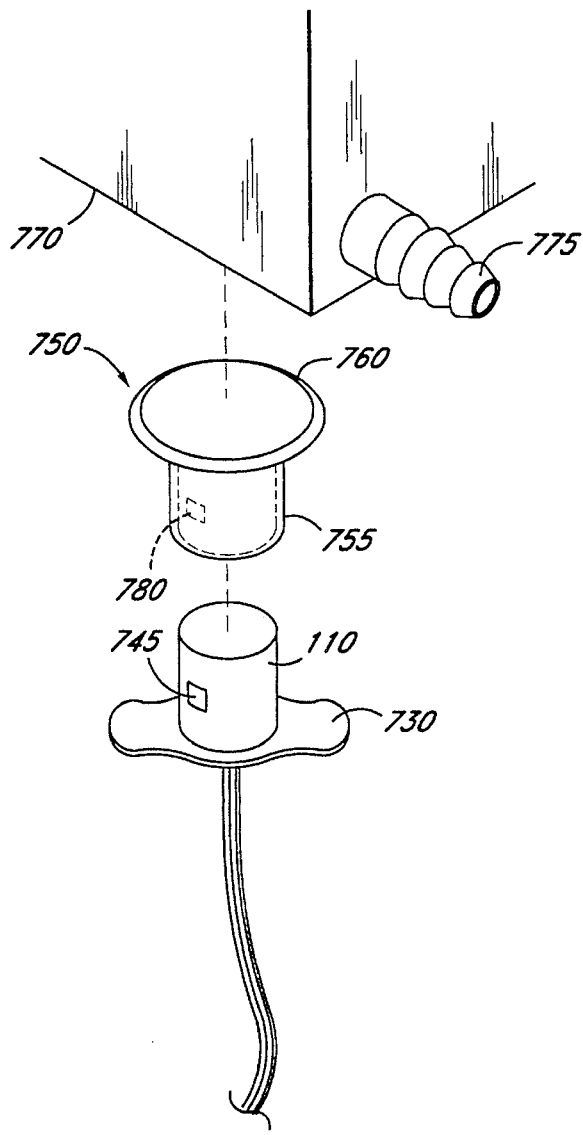

In the embodiment shown in FIG. 7b, an adaptor 750 is made of a durable plastic, and includes a receiving structure such as a cylinder 755 and a fastening surface 760. The fastening surface 760 can be attached to the base of a container 770, near an outlet port 775 by means of a suitable epoxy, two sided tape, or the like, so long as the adhesive has either minimal or no gaseous inclusions. The transducer 110 having the gripping mounts 730 and the photo-diode 745 is securable within the receiving cylinder 755. The receiving cylinder 755 also includes a bar code 780 (shown in phantom) which is situated on the inside surface of the cylinder 755. The bar code 780 is positioned so that the photo-diode 745 coincides with the bar code 780 when the transducer 110 is fastened within the cylinder 755. Thus, the photo-diode 745 is able to detect the bar code 780 by means of the electronic circuitry 150 as described above. A variety of alternatives to the bar code can be devised, as will be apparent to one of skill in the art. For example, in an embodiment where the receiving structure 755 and transducer have complementary surface structures, the location, rather than the content of the bar code or other indicator, can provide the desired information.

As illustrated above, machine readable identification on the adaptor is not necessary for all applications of the present invention. For example, the adaptor can be integrally formed with the container at the point of fabrication. The transducer can be mounted on the adaptor, and the instrument calibrated all prior to sale. In this circumstance, the need to avoid adaptor-container mismatches is eliminated.

In some instances when the adaptor is separate from the container, the adaptor and container will be assembled at the point of manufacture. Assembly personnel or robotics can be supplied only with a particular container and appropriate adaptor, thereby eliminating the possibility of mismatch. Alternatively, the containers and adaptors can be color coded or provided with other indicia which are human readable to insure that the appropriate adaptor and container are matched.

Machine readable indicia and/or complementary surface structures on the container and adaptor are most desirable in an embodiment of the fluid volume sensor system intended for installation or adjustment by the end user. For example, a given adaptor can be provided with surface structures which physically prevent the attachment of that adaptor to any but corresponding surface structures on the appropriate container. These structures can take any of a variety of forms as will be readily understood by one of skill in the art. For example, one or more pins on a first surface can be required to align with one or more corresponding holes on the second surface before the first and second surfaces can be sonically engaged. Alternatively, keyways can be provided which will only receive a projection having the appropriate configuration. Also, simply conforming the adaptor mating surface to the non planar exterior of the container will work if each different volume container has a different configuration.

B. Adaptors for Existing Outlet Ports

Many liquid containers, especially those used in the medical field, have at least one outlet port which is located at the lowest point of the container. In a high percentage of these containers, this outlet port points downwards, i.e., the direction of flow of a liquid out of the container through this port is roughly perpendicular to the surface of the liquid in the container, when a liquid is present in the container. Outlet ports such as these provide a liquid path or "view" from the outlet end of the port up to the surface of the liquid, and in many containers this view is unobstructed by gas or other media which would block the passage of an ultrasonic signal from the port to the surface of the liquid. This view can therefore be utilized by ultrasonic volume or level sensing devices for determining the volume or level of a liquid in such containers.

Thus, in accordance with another aspect of the present invention, an adaptor for mounting an ultrasonic transducer onto the liquid outlet port of a container is provided. In one embodiment, shown in FIG. 3c, such an adaptor can be integrally formed with the outlet port 283 of a container. However, when such an integral adaptor is not provided on a container, an adaptor according to an alternate embodiment of the present invention can be fitted onto the outlet port of a container.

Referring to FIGS. 9–13, the adaptor 900 of this aspect of the present invention is composed of several components. One of these components can be referred to as the central hollow member 910. As its name implies, the central hollow member 910 should be hollow, that is, there should be a space within the member and it should have at least one opening 920 to allow the passage of a liquid from the container into the central hollow member 910 so that an ultrasonic signal can be propagated from the adaptor 900 into the container. Typically, this member 910 will have two openings and will be tubular in shape. Although the shape of the central hollow member 910 is not critical, it is important that the inner surface 912 of the central hollow member 910 not be formed so as to allow a gas interface to obstruct the path of an ultrasonic signal traveling through adaptor 900 to the surface of a liquid in the container to which the adaptor 900 is attached, or traveling back therefrom.

The central hollow member 910 is typically formed from a relatively rigid material, such as polycarbonate plastic. The central hollow member 910 should in any case be formed from a material which is compatible with the liquid held in the container. For example, if the container holds water or an aqueous solution, the central hollow member 900 can be made from any of a variety of plastics, such as PVC, acrylic, polypropylene, or polycarbonate. The material used to form the central hollow member 910 should also be as thin as possible, preferably less than 0.250 inches in thickness, and more preferably less than 0.100 inches in thickness, in order to assist in the ease of manufacturing.

When the adaptor of the present invention is being used in a medical setting, bio-compatible plastic materials such as polystyrene, acrylic, or polycarbonate are preferred because they are inexpensive and can be disposed of after use. The disposability of the adaptor of the present invention is an important consideration when the adaptor is used in a medical setting for reasons of sanitation and hygiene. It is also preferred that adaptors used in a medical setting be clear (i.e., see-through) so that the passage of a medical liquid through the adaptor can be observed.

The ports to which the adaptor 900 can be attached typically have barbed fittings to which flexible tubing can be connected. One means of connecting the adaptor 900 to such ports involves the use of a separate piece of flexible tubing (not shown) which is attached to the port receiving end 930 of the central hollow member 910. The flexible tubing should have sufficient elasticity so as to be able to secure the adaptor 900 to the outlet port of a container. The flexible piece of tubing should also be sized in diameter so that it is able to fit over the lower, narrower barbs of the barbed fitting of an outlet port and then grip the barbs which are higher up and wider. In an alternative embodiment, the flexible piece of tubing can also be secured to the inner surface of an outlet port when attachment to the outer surface of the port is impractical, with attachment being made by means of adhesives, a mechanical fitting, or other means known to those of skill in the art.

The end of the flexible tubing attached to the port receiving end 930 of the adaptor 900 can be secured to either inner surface 912 or outer surface 914 of the port receiving end 930 of the central hollow member 910. Securing the piece of flexible tubing can be accomplished by any means known to those of skill in the art, such as through the use of an adhesive or a mechanical fitting. In an alternate embodiment, one piece of flexible tubing can be attached to the inner surface 912 of the port receiving end 930 of the central hollow member 910, and another piece of flexible tubing can be attached to the outer surface 914, in order to assure the proper positioning of the adaptor 900.

In a further embodiment, the central hollow member 910 can be made of a relatively thin, flexible material. The flexibility of the central hollow member 910 would allow its port receiving end 930 to fit over and grip a container's outlet port without the use of a separate piece of flexible tubing. Thus, the central hollow member 910 itself can be used to connect the adaptor 900 to a container. In this embodiment, the port receiving end 930 of the central hollow member 910 can alternatively be fit to the inner surface of the outlet port of the container. As the inner portion of most container outlet ports are smooth, this approach may require the use of an adhesive to provide a rigid connection between the outlet port of the container and the outer surface 914 of the port receiving end 930 of the adaptor 900. Other ways of attaching the central hollow member 910 or a piece of flexible tubing connected thereto to a particular port, including ports which do not have barbed fittings, can also be used.

The adaptor of the present invention can further comprise a component for directing liquid out of the adaptor 900. This component, like the central hollow member 910, is also hollow and is referred to herein as a medial hollow member 950. The medial hollow member 950 has at least two openings. One of these openings is in fluid communication with the interior of the central hollow member 910, while the other is an outlet opening 952 to which a liquid conduit, such as a piece of flexible tubing, can be connected. One or more other outlet openings can also be provided in the medial hollow member 950.

The medial hollow member 950 is typically, although not necessarily, made from the same material as the central hollow member 910, and is also typically made from a relatively rigid material such as polycarbonate plastic. When the adaptor 900 is constructed from a plastic material, the medial hollow member 950 and central hollow member 910 are preferably formed together as a unit, such as by injection molding. The medial hollow member 950 can also, of course, be affixed to the central hollow member 910 in other ways known to the art, such as with adhesives or by means of a mechanical fitting.

The medial hollow member 950 effectively replaces the outlet port of a container to which the adaptor 900 is attached and allows the passage of liquids out of the adaptor 900. Typically, the medial hollow member 950 protrudes from the central hollow member in a "T" or "Y" configuration, that is, the central axis of the medial hollow member 950 is a straight line so that the medial hollow member 950 protrudes axially from the central hollow member 910. FIGS. 3c and 10–13 illustrate medial hollow members 950 having such "Y" configurations.

Thus, a liquid flowing out of a container's outlet port and through the medial hollow member 950 is diverted at a given angle away from the vertical axis of the container's outlet port. Looking now at FIG. 10, this angle is, roughly, the angle 958 formed by the vertical axis of the outlet port, which is normally approximately the same as the central axis 954 of the central hollow member 910, and by the central axis 956 of the medial hollow member 950. In a "T" configuration (not shown in the Figures), this angle is 90°. Preferably, however, the medial hollow member 950 is positioned so that the angle 958 is less than 90°. An angle 958 of less than 90° should generally allow a smoother (i.e., more laminar) liquid flow from the central hollow member through the medial hollow member. For this reason, angles 958 of 45°, 30°, 15°, 10°, 5°, or even less are preferred.

Another component of the adaptor 900 of the present invention is a seat 960 located in a transducer receiving end 940 of the central hollow member 910. This seat 960 is usually formed as an integral part of the central hollow member 910 and is configured so as to be able to receive an ultrasonic transducer 970. The outer surface 962 of the seat 960 is, moreover, configured so as to be able to form a flush fit with the face 972 of the ultrasonic transducer 970, so that an ultrasonic signal can be sent by the transducer 970 through the seat 960 and into a liquid present in the adaptor 900, i.e. so that the transducer 970 is in sonic communication with the adaptor 900.

The transducer 970 can be secured to the seat 960 of the adaptor 900 so as to provide an ultrasonic coupling (i.e., put the transducer in sonic communication with a liquid in the adaptor 900) in any of a number of ways known to those of skill in the art. For example, the transducer 970 can be mechanically secured to the seat 960, such as through a bayonet fitting, or through threads in the transducer 970 which screw into grooves in the seat 960 (not shown in Figures). When mechanically fitting the transducer to the seat of the adaptor, a coupling gel, such as glycerine or silicone oil, can be placed between the transducer 970 and the seat 960 in order to eliminate any pockets of gas between the transducer 970 and the adaptor 900. Alternatively, as described previously, a deformable, resilient material such as latex can be placed between the face 972 of the transducer 970 and the outer surface 962 of the seat 960.

Another means of reversibly mounting the transducer 970 onto the adaptor 900 is through the use of a magnetic material. Preferably, when a magnetic material is being used to attach the transducer 970 to the adaptor 900, both the face 972 of the transducer 970 and the outer surface 962 of the seat 960 are formed from magnetic materials of opposite polarity. More preferably still, a plurality of magnets are included in each of the face 972 of the transducer 970 and the outer surface 962 of the seat 960, as shown in FIGS. 19, and at least one of these magnets is of the opposite polarity compared to the other magnet or magnets in the transducer 970 or in the seat 960. Thus, if magnetic materials 1202 and 1204 (and likewise magnetic materials 1206 and 1208) are of opposite polarities, and if the magnetic materials 1202 and 1208 have the same polarity, then the transducer 970 will only attach to the container (shown in outline) if the magnetic material 1202 is aligned with magnetic material 1206 and the magnetic material 1204 is aligned with magnetic material 1208.

The transducer 970 can also be bonded to the adaptor 900, such as with epoxy glues, hot-melt thermoplastics, or other adhesives. In one embodiment, the transducer 970 can also be embedded in the adaptor 900, as shown in FIG. 9A. In addition, the transducer can be reversibly mounted through the use of a pressure-sensitive adhesive. For example, a double sided tape can be used. Materials having gaseous inclusions, such as foamed materials, tend to dampen the propagation of an ultrasonic signal, however, and therefore should not be used.

Various adaptor configurations are possible. However, it is important that the transducer 970 be mounted onto the adaptor 900 so that the transducer's ultrasonic signal travels in a primarily perpendicular direction with respect to the container's liquid surface. Therefore, the transducer face 972 should be substantially parallel to the surface of a liquid in any container to which the adaptor 900 is fitted. The ultrasonic signal should also be able to travel from the port to the surface of a liquid in any such container in a direction which is primarily parallel to the central axis of the container's outlet port.

One problem which can affect the transmission of an ultrasonic signal through the central hollow member 910 of the adaptor 900 is the formation of gas bubbles. Since ultrasonic signals are reflected at a liquid-gas interface, and since bubbles contain such interfaces, gas bubbles which form in the central hollow member 910 can potentially interfere with the operation of an ultrasonic fluid volume sensor attached to the adaptor 900.

Gas bubbles can form in liquids as a result of turbulence, and it is believed that one possible cause of turbulence in the adaptor of the present invention could be the change in direction of the flow of a liquid from the central hollow member 910 into the medial hollow member 950. In order to reduce the turbulence generated by the change in direction in the flow of a liquid through this junction, several alternative designs of the adaptor of the present invention can be used. One such alternative is illustrated in FIG. 9. In this embodiment, the change in direction of the liquid flowing through the central hollow member 910 into the medial hollow member 950 is minimized.

Another embodiment designed to minimize turbulence and thus the generation of gas bubbles in the adaptor 900 is shown in FIG. 10. In this embodiment, the medial hollow member 950 extends axially from the central hollow member 910 at a point which is distal from the seat 960, thus creating a "pocket" 942. In this pocket 942, liquid will remain relatively undisturbed, since the main current of liquid flow is through the medial hollow member 950 and since the change in direction of that liquid flow occurs at a point above the seat 960. The pocket 942 thereby creates a buffer of relatively non-turbulent or stagnant liquid without gas bubbles. In situations in which such stagnant liquid is undesirable, such as certain medical applications, however, the embodiment of FIG. 10 is not preferred.

Figure 11:
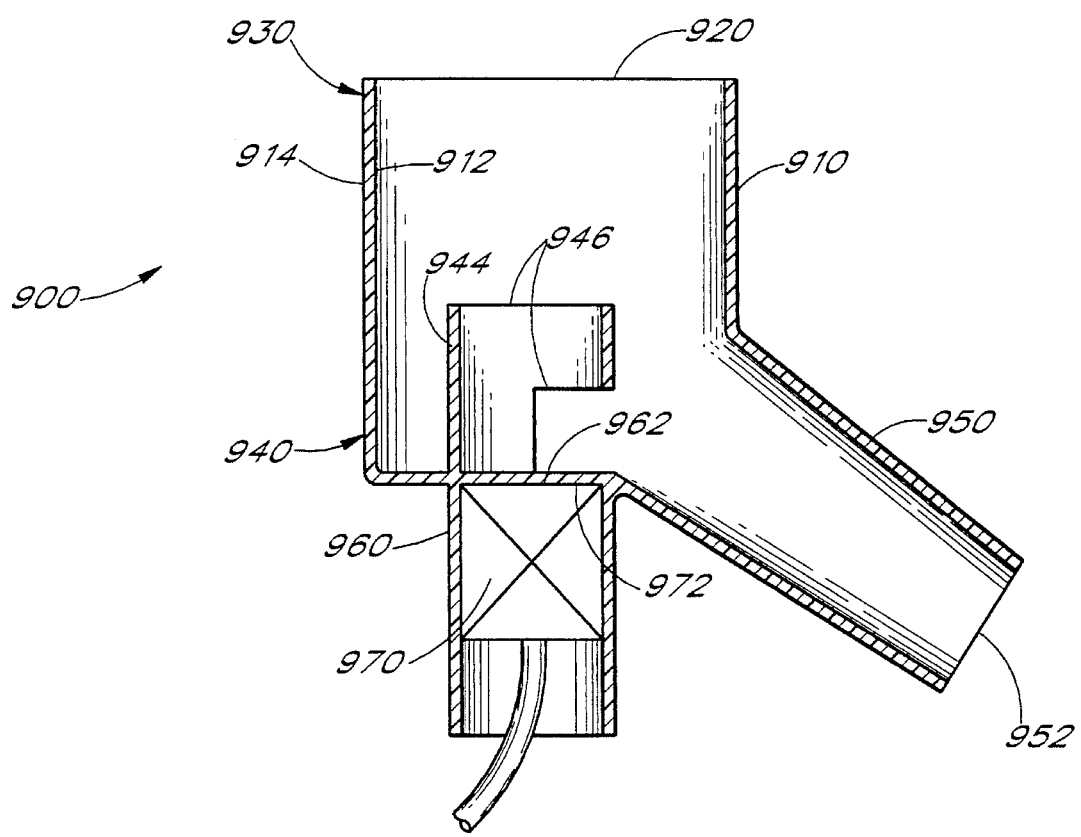
FIG. 11 is a cross-sectional view of an embodiment of the adaptor having a shield for reducing the effects of liquid turbulence on an ultrasonic signal propagated through the adaptor.

Another way of reducing the possibility of ultrasonic signal interference from gas bubbles is to shield the path through which the ultrasonic signal travels. For example, as shown in FIG. 11, a shield 944 can be formed around the signal path so that gas bubbles generated by turbulence below the upper extent of the shield 944 flow around the shield 944 and into the medial hollow member 950 without passing through the signal path. Openings 946 should be provided in the shield 944 to allow liquid to flow through the shield 944, thereby reducing any turbulence which might be generated by the presence of the shield itself. Preferably, the shield 944 provides multiple openings to allow the passage of liquid. The shield 944 should encompass at least a portion of the signal path of an ultrasonic signal originating in the transducer 970 in order to protect the ultrasonic signal.

Figure 12:
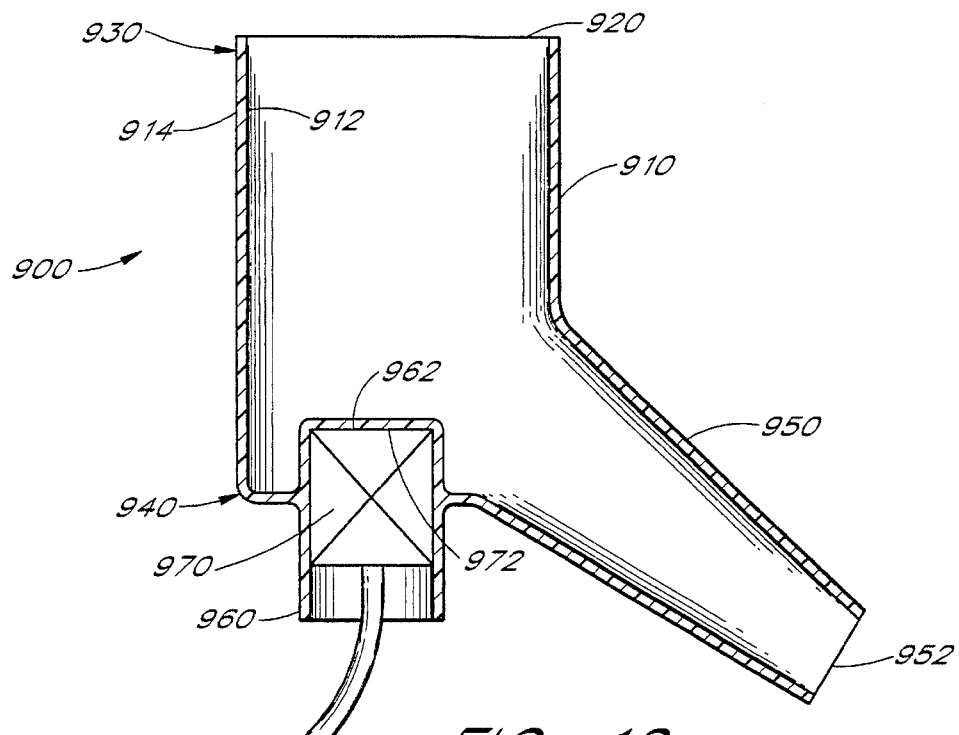
FIG. 12 is a cross-sectional view of another embodiment of the adaptor in which the seat for the ultrasonic transducer is raised relative to the transducer receiving end of the adaptor in order to reduce the effects of liquid turbulence on an ultrasonic signal propagated through the adaptor.

In another embodiment of the adaptor for reducing signal interference due to gas bubbles, shown in FIG. 12, the seat 960 housing the transducer 970 can be raised up beyond the end of the transducer receiving end 940 in order to place the beginning of the ultrasonic signal path beyond the area where gas bubbles are most likely to form. This strategy for reducing signal interference is similar to that of the embodiment shown in FIG. 11, namely placing the point at which an ultrasonic signal might encounter gas bubbles above the point where such bubbles are likely to form.

Figure 13:
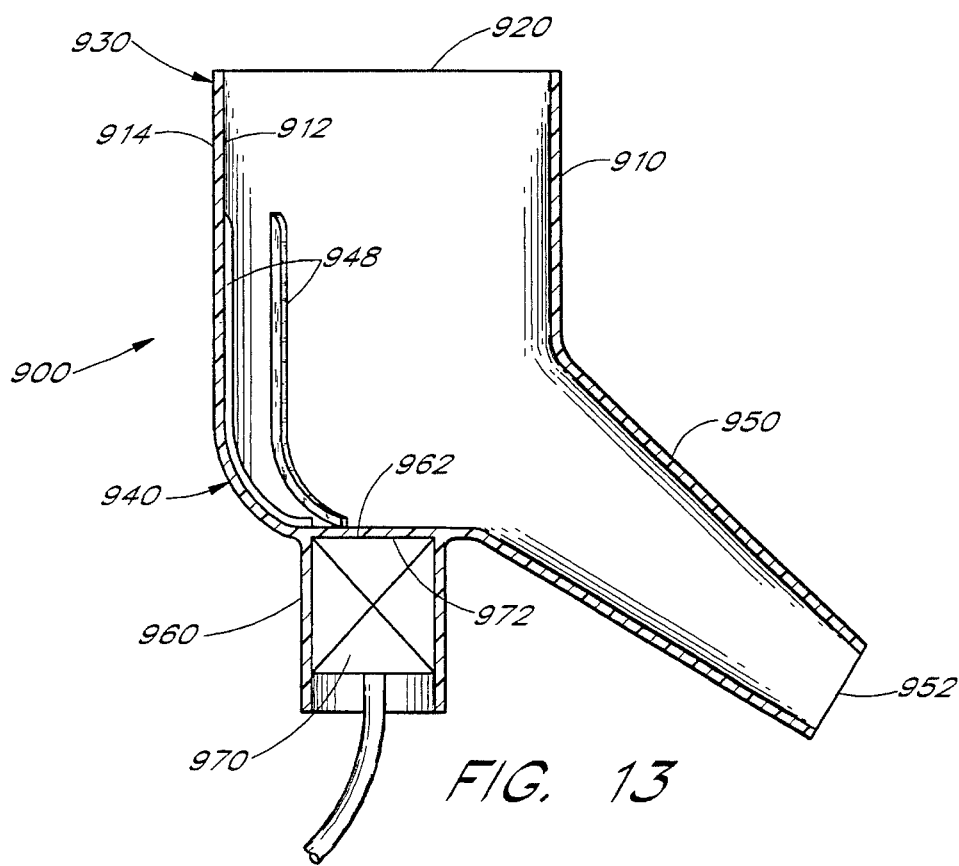
FIG. 13 is a cross-sectional view of an embodiment of the adaptor having channels for directing liquid flow in the adaptor and for reducing the effects of liquid turbulence on an ultrasonic signal propagated through the adaptor.

A further embodiment, shown in FIG. 13, reduces turbulence in the adaptor 900 by streamlining the flow of liquid in the adaptor. In this embodiment, channel guides 948 promote laminar flow and thus reduce turbulence. In addition, the channel guides 948 help to compartmentalize any turbulence which does occur in areas lying between such guides. In this way, the amount of bubble formation can be reduced.

Other means of reducing air bubbles in the adaptor 900 can, of course, also be employed. For example, a screen mesh such as a debubbling screen (not shown in the Figures) can be placed in and/or around the signal path of the adaptor 900 to prevent bubbles from entering the path. A defoamer such as antifoam (sold by Dow Corning) can also be placed in liquid passing through the adaptor 900 to prevent the formation of gas bubbles.

In order to control the passage of liquids through the adaptor 900, a valve (not shown in the Figures) can also be included in the medial hollow member 950. Alternatively, such a valve can be included in the central hollow member 910. Any of a number of valves known to those of skill in the art can be used, such as a pinch valve controlled by a solenoid. In one embodiment, one or more valves in the adaptor 900 can be controlled by the electronic circuitry of a fluid level or volume sensing device, as described elsewhere herein.

The following example illustrates one embodiment of the adaptor of the present invention and its use:

EXAMPLE 1

Using an Adaptor to Detect the Fluid Volume of a Container

An adaptor made of 0.070 inch-thick acrylic and having a flexible central hollow member which has a central diameter of approximately ⅜" is fit onto the barbed fitting of an outlet port of a container, with the barbed fitting being approximately ⅜" in diameter. The outlet port is located at the bottom of the container and is positioned at a 90° angle with respect to the surface of the liquid in the container. An ultrasonic transducer connected to a microprocessor is attached to the seat of the adaptor with 3M brand adhesive tape such that the face of the transducer is approximately parallel to the surface of the liquid in the container. The configuration of the container is inputted into the microprocessor, and an ultrasonic signal is then sent from the transducer through the adaptor, through the outlet port of the container, and up to the interface of the liquid and the air. When the signal is reflected back and received by the transducer, the travel time of the signal is translated by the microprocessor into liquid volume data.

The foregoing description should be construed as merely illustrative and in no way restrictive to the spirit and scope of the present invention. For example, the circuitry 150 can be implemented using specialized control and computation circuitry, or by means of computer software, rather than the CPU 400. Also, the LUT 430 can be implemented using any kind of memory unit which provides a desired output in response to a known input. Furthermore, the adaptor can be implemented in a variety of embodiments which allow the transducer to be employed with any number of container configurations. Moreover, the adaptor can also include a region which is permanently magnetized, or any similar means of conveying data, so that the adaptor 125 is capable of indicating the configuration of the container to which the adaptor is attached. The adaptor can also include electronic circuitry (e.g., an addressable memory chip) which is capable of transmitting data to the CPU via the transducer 110. Accordingly, the scope of the invention, including all embodiments and their equivalents, should be understood in light of the appended claims.

We claim:

1. A container for liquids, said container comprising an upper end and a lower end, wherein said container further comprises:

a seat in said lower end of said container;

an ultrasonic transducer affixed to and in ultrasonic communication with said seat, said transducer being positioned in said seat such that an ultrasonic signal generated by said transducer travels approximately perpendicular to the surface of a liquid in said container when said liquid is present in said container; and a reversible physical connection which provides an electrical link between said ultrasonic transducer and electronic circuitry capable of directing said transducer to generate an ultrasonic signal.

2. The container of claim 1, wherein said transducer, said seat, and said reversible physical connection are integrally molded into said container.

3. The container of claim 2, wherein said transducer is embedded in said container.

4. The container of claim 1, wherein said container is made from a plastic material.

5. The container of claim 1, wherein said reversible connection comprises a socket.

6. A flexible container for a liquid, said container having an upper end and a lower end, said container comprising:

a seat in the lower end of said container for engaging an ultrasonic transducer;

a hollow member having an interior and an exterior positioned above said seat inside said container, said hollow member being rigid and encompassing an ultrasonic signal path on the interior of said hollow member, wherein said hollow member extends from said lower end of said container to said upper end of said container, said signal path extending upward from said seat approximately perpendicular to the surface of a liquid when said liquid is present in said container, said hollow member further permitting liquid communication between the interior of said hollow member and the exterior of said hollow member.

7. A semi-rigid container for liquids, said container having an upper end and a lower end, said container comprising:

a rigid wall extending from said lower end of said container to said upper end of said container;

a flexible wall attached to said rigid wall;

a seat in the lower end of said container for engaging an ultrasonic transducer;

means for providing an ultrasonic signal path from the lower end of said container to the upper end of said container, said signal path extending upward from said seat approximately perpendicular to the surface of a liquid when said liquid is present in said container.

8. The container of claim 7, wherein said means for providing an ultrasonic signal path from the lower end of said container to the upper end of said container comprises:

a hollow member having an interior and an exterior positioned above said seat inside said container, wherein said hollow member is rigid and encompasses said ultrasonic signal path, and wherein said hollow member extends from said lower end of said container to said upper end of said container, said hollow member permitting fluid communication between the interior of said hollow member and the exterior of said hollow member.

9. An adaptor for mounting an ultrasonic transducer onto a port in a container for a liquid, said container further having an upper end and a lower end, said port being located in the lower end of said container, said adaptor comprising:

a central hollow member having an inner surface and an outer surface, said central hollow member having an opening at a port receiving end for connecting said adaptor to said port, said central hollow member further having a transducer receiving end;

a seat in said central hollow member for engaging said ultrasonic transducer, said seat having an outer surface for contacting a transducer, wherein said outer surface is substantially parallel to the surface of said liquid in said container when said liquid is present in said container; and a medial hollow member connected to said central hollow member, wherein said medial hollow member and said central hollow member are in fluid communication.

10. The adaptor of claim 9, wherein said medial hollow member is connected to said central hollow member at a point between said seat for engaging said ultrasonic transducer and said port receiving end of said adaptor.

11. The adaptor of claim 10, wherein said medial hollow member is connected to said central hollow member at a point which is distal with respect to said seat, thereby creating a pocket between said medial hollow member and said seat.

12. The adaptor of claim 9, further comprising a shield on the interior of said central hollow member extending upward from said seat of said central hollow member, said shield encompassing said signal path.

13. The adaptor of claim 9, wherein said outer surface of said seat is positioned in said central hollow member distally with respect to said transducer receiving end of said central hollow member.

14. The adaptor of claim 9, wherein said medial hollow member extends axially from said central hollow member at an angle of 90° or less with respect to the central axis of said central hollow member.

15. The adaptor of claim 14, wherein said medial hollow member extends from said central hollow member at an angle of 45° or less with respect to the central axis of said central hollow member.

16. The adaptor of claim 9, additionally comprising an ultrasonic transducer attached to said seat in said transducer receiving end of said central hollow member.

17. The adaptor of claim 16, wherein said transducer is embedded in said seat.

18. The adaptor of claim 17, additionally comprising a reversible physical connection which provides an electrical link between said ultrasonic transducer and electronic circuitry capable of directing said transducer to generate an ultrasonic signal.

19. The adaptor of claim 16, wherein said transducer is attached to said seat by means of a mechanical fitting.

20. The adaptor of claim 19, wherein a layer of resilient, deformable material is positioned between said transducer and said seat.

21. The adaptor of claim 20, wherein said material is latex.

22. The adaptor of claim 19, wherein a coupling gel is positioned between said transducer and said seat.

23. The adaptor of claim 16, wherein said transducer is attached to said seat through a magnetic coupling.

24. The adaptor of claim 23, wherein said seat contains a plurality of magnets in a predetermined configuration, wherein at least one of said plurality of magnets has a polarity which is opposite that of the remaining magnets of said seat, and wherein the face of said transducer also contains a plurality of magnets, the configuration of said plurality of magnets of said transducer being the mirror image of said predetermined configuration of said plurality of magnets of said seat, so that each magnet of said transducer can align with a magnet of said seat when said seat is contacted with the face of said transducer, and wherein the polarity of each of said plurality of magnets of said transducer is opposite the polarity of the magnet of said seat with which it can align when said seat and said transducer are brought into contact.

25. The container of claim 1, wherein said reversible physical connection comprises a magnetic material.

26. The container of claim 1, wherein said reversible physical connection comprises a plurality of magnetic materials.

27. An adaptor for magnetically mounting an ultrasonic transducer onto a lower end of a container for a liquid, said adaptor comprising:

a seat for engaging said ultrasonic transducer, said seat having an outer surface for contacting said ultrasonic transducer, wherein said outer surface is substantially parallel to the surface of said liquid in said container when said adaptor is mounted onto said container and liquid is present in said container; and a plurality of magnetic materials in said seat, wherein said plurality of magnetic materials align with magnetic materials of opposite polarity on a transducer in order to attach said transducer to said seat.

28. An adaptor for mounting an ultrasonic transducer onto a lower end of a container for a liquid, said adaptor comprising:

a seat for engaging said ultrasonic transducer, said seat having an outer surface for contacting said ultrasonic transducer, wherein said outer surface is substantially parallel to the surface of said liquid in said container when said adaptor is mounted onto said container and liquid is present in said container; and a reversible physical connection for attaching said ultrasonic transducer to said seat.

29. The adaptor of claim 28, wherein said reversible physical connection comprises a socket.

30. The adaptor of claim 28, wherein said reversible physical connection comprises a magnetic material.

* * * * *